US008236344B2

(12) United States Patent
Tirrell et al.

(10) Patent No.: US 8,236,344 B2
(45) Date of Patent: *Aug. 7, 2012

(54) ENGINEERED PROTEINS, AND METHODS OF MAKING AND USING

(75) Inventors: David A. Tirrell, Pasadena, CA (US); Daniel M. Schwartz, San Francisco, CA (US); Paul J. Nowatzki, Pasadena, CA (US); Robert H. Grubbs, South Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 1113 days.

This patent is subject to a terminal disclaimer.

(21) Appl. No.: 11/757,990

(22) Filed: Jun. 4, 2007

(65) Prior Publication Data

US 2010/0233242 A1 Sep. 16, 2010

Related U.S. Application Data

(63) Continuation of application No. 11/040,130, filed on Jan. 21, 2005, now Pat. No. 7,229,634.

(60) Provisional application No. 60/538,844, filed on Jan. 23, 2004, provisional application No. 60/552,029, filed on Mar. 10, 2004.

(51) Int. Cl.
*A61F 2/14* (2006.01)
*A61F 2/16* (2006.01)
*A61K 38/39* (2006.01)

(52) U.S. Cl. ......................... 424/427; 530/353; 623/6.11

(58) Field of Classification Search .................. None
See application file for complete search history.

(56) References Cited

U.S. PATENT DOCUMENTS

| 1,999,446 | A | 4/1935 | Delano |
| 3,129,361 | A | 4/1964 | Berenbaum |
| 4,264,155 | A | 4/1981 | Miyata |
| 4,941,333 | A | 7/1990 | Blessing |
| 7,229,634 | B2 | 6/2007 | Tirrell et al. |
| 2002/0028243 | A1 | 3/2002 | Masters |

FOREIGN PATENT DOCUMENTS

| JP | 56-011430 | 2/1981 |
| JP | 2006-533468 | 11/2003 |
| WO | 86/05097 | 9/1986 |
| WO | WO-95/13764 | 5/1995 |
| WO | 01/87267 | 11/2001 |
| WO | 02/090528 | 11/2002 |

OTHER PUBLICATIONS

Lee, C-H., et al. 1995 The EMBO Journal 14(20): 5006-5015.*
Obara, M., et al. 1988 Cell 53: 649-657.*
Chaouk et al., "New Porous Perfluoropolyether Membranes," *Journal of Applied Polymer Science*, 80: 1756-1763, 2001.
Di Zio et al., "Mechanical Properties of Artificial Protein Matrices Engineered for Control of Cell and Tissue Behavior," *Macromolecules*, 36: 1553-1558, 2003.
Evans et al., "Epithelialization of a Synthetic Polymer in the Feline Cornea: a Preliminary Study," *Investigative Ophthalmology & Visual Science*, 41(7): 1674-1680, 2000.
Evans et al., "Progress in the Development of a Synthetic Corneal Onlay," *Investigative Ophthalmology & Visual Science*, 43(10): 3196-3201, 2002.
Giancotti et al., "Integrin Signaling," *Science*, 285: 1028-1032, 1999.
Gipson et al., "Hemidesmosomes and Anchoring Fibril Collagen Appear Synchronously during Development and Wound Healing," *Developmental Biology*, 126: 253-262, 1988.
Gipson et al., "Reassembly of the Anchoring Structures of the Corneal Epithelium during Wound Repair in the Rabbit," *Investigative Ophthalmology & Visual Science*, 30(3): 425-434, 1989.
Halstenberg et al., "Biologically Engineered Protein-*graft*-Poly(ethylene glycol) Hydrogels: A Cell Adhesive and Plasmin-Degradable Biosynthetic Material for Tissue Repair," *Biomacromolecules*, 3: 710-723, 2002.
Hicks et al., "Clinical results of implantation of the Chirila keratoprosthesis in rabbits," *Br. J. Ophthalmol.*, 82: 18-25, 1998.
Hong et al., "Structure of an Elastin-Mimetic Polypeptide by Solid-State NMR Chemical Shift Analysis," *Biopolymers*, 70: 158-168, 2003.
Johansson et al., "Fibronectin-Integrin Interactions," *Frontiers in Bioscience*, 2: 126-146, 1997.
Jones et al., "Hemidesmosomes: Extracellular Matrix/Intermediate Filament Connectors," *Experimental Cell Research*, 213: 1-11, 1994.
Lass et al., "Epikeratoplasty: The Surgical Correction of Aphakia, Myopia, and Keratoconus," *Ophthalmology*, 94: 912-925, 1987.
Legeais et al., "A second generation of artificial cornea (Biokpro II)," *Biomaterials*, 19: 1517-1522, 1998.
Liu et al., "Comparative Cell Response to Artificial Extracellular Matrix Proteins Containing the RGD and CS5 Cell-Binding Domains," *Biomacromolecules*, 5: 497-504, 2004.
Rao et al., "Specular Microscopy of Corneal Epithelium After Epikeratophakia," *Americal Journal of Ophthalmology*, 103: 392-396, 1987.
Rodrigues et al., "Clinical and Histopathologic Changes in the Host Cornea After Epikeratoplasty for Keratoconus," *Americal Journal of Ophthalmology*, 114: 161-170, 1992.
Ruoslahti et al., "Arg-Gly-Asp: A Versatile Cell Recognition Signal," *Cell*, 44: 517-518, 1986.
Sweeney et al., "Nutritional Requirements of the Corneal Epithelium and Anterior Stroma: Clinical Findings," *Investigative Ophthalmology & Visual Science*, 39(2): 284-291, 1998.
Sweeney et al., "A Comparison of Biological Coatings for the Promotion of Corneal Epithelialization of Synthetic Surface In Vivo," *Investigative Ophthalmology & Visual Science*, 44(8): 3301-3309, 2003.
Tisdale et al., "Development of the Anchoring Structures of the Epithelium in Rabbit and Human Fetal Corneas," *Investigative Ophthalmology & Visual Science*, 29(5): 727-736, 1988.

(Continued)

*Primary Examiner* — Marsha Tsay
(74) *Attorney, Agent, or Firm* — Steinfl & Bruno, LLP

(57) ABSTRACT

The present invention provides engineered proteins and biomedical products made from the engineered proteins. The biomedical products include lenses useful for ophthalmic purposes.

11 Claims, 5 Drawing Sheets

OTHER PUBLICATIONS

Trabbic-Carlson et al., "Swelling and Mechanical Behaviors of Chemically Cross-Linked Hydrogels of Elastin-like Polypeptides," *Biomacromolecules*, 4: 572-580, 2003.

Urry et al., "Elastic Protein-based Materials in Tissue Reconstruction," *Bioartificial Organs: Science, Medicine, and Technology*, Prokop et al., eds., The New York Academy of Sciences, vol. 831, pp. 32-46, 1997.

Urry, "Physical Chemistry of Biological Free Energy Transduction as Demonstrated by Elastic Protein-Based Polymers," *J. Phys. Chem. B.*, 101: 11007-11028, 1997.

Xie et al., "A thin glycoprotein coating of a synthetic lenticule does not cause nutritional deficiency of the anterior cornea," *Current Eye Research*, 18(5): 335-341, 1999.

Xie et al., "Artificial Cornea: Towards a Synthetic Onlay for Correction of Refractive Error," *Bioscience Reports*, 21(4): 513-536, 2001.

Lee, J., Macosko, C. and Urry, D.W. Elastomeric Polypentapeptides Crosslinked into Matrixes and Fibers. *Biomacromolecules* Jan. 31, 2001;2, 170-179.

Cheung, Resident's Day Talk (presentation), Resident's Day, UCSF, Ophthalmology, Mar. 11, 2004.

Hanna et al., "Cell production and migration in the epithelial layer of the cornea," *Arch. Ophthalmol.*, 64: 536, 1960.

Heilshorn et al., "Cell-Binding Domain Context Affects Cell Behavior on Engineered Proteins," *Biomacromolecules*, 6: 318-323, 2005.

Heilshorn et al., "Endothelial cell adhesion to the fibronectin CS5 domain in artificial extracellular matrix proteins," *Biomaterials*, 24: 4245-4252, 2003.

Panitch et al., "Design and Biosynthesis of Elastin-like Artificial Extracellular Matrix Proteins Containing Periodically Spaced Fibronectin CS5 Domains," *Macromolecules*, 32: 1701-1703, 1999.

Welsh et al., "Engineering the Extracellular Matrix: A Novel Approach to Polymeric Biomaterials. I. Control of the Physical Properties of Artificial Protein Matrices Designed to Support Adhesion of Vascular Endothelial Cells," *Biomacromolecules*, 1: 23-30, 2000.

Kobatake, E., et al 2000 Biomacromolecules 1: 382-386.

Sergel, T.A., et al. 2000 J. Virology: 51-1-5107.

Yuan, S-M., et al. Proteins: Structure, Function, and Genetics 30: 136-143, 1998.

Dupont, D., et al. Biocompatibility of human collagen type IV intracorneal implants. Cornea; Dec; 8(4): 251-8 (1989).

Evans, M.D., et al. Persistent adhesion of corneal epithelial tissue on synthetic lenticules in vivo. Aust N Z J Ophthalmol.; 26 (Suppl.) 1: S40-3 (1998).

Iskander, N.G., et al. Postoperative complications of laser in situ keratomileusis. Curr Opin Ophthalmol; 11: 273-279 (2000).

Kornmehl, E.W., et al. In vivo evaluation of collagen corneal allograft derived from rabbit dermis. J Refract Surg; 11: 502-506 (1995).

Latkany, R., et al. Plasma surface modification of artificial corneas for optimal epithelialization. J Biomed Mater Res; 36: 29-37 (1997).

Leibowitz, H. M., et al. Progress in the development of a synthetic cornea. Prog Retinal Eye Res; 13: 605-21 (1994).

McCarey, B.E., et al. Collagen onlay epikeratoplasty after one year in the monkey model. Invest Ophthalmol Vis Sci; 40(4); S511 (1997). [ARVO abstract 2362].

McDonald, M.B. The future direction of refractive surgery. J Refract Surg; 4: 158-168 (1988).

McDonald, M.B. (1988). Onlay Lamellar Keratoplasty. In H.E. Kaufman, et al. (Eds.), *The Cornea* (pp. 697-711). New York: Churchill Livingstone.

Nicol, A., et al. Cell adhesion and growth on synthetic elastomeric matrices containing Arg-Gly-Asp-Ser-3. J Biomed Mater Res.; 26(3): 393-413(Mar. 1992).

National Center for Health Statistics, Poe, G.S. Eye-Care Visits and Use of Eyeglasses or Contact Lenses, United States, 1979 and 1980. Vita Health Statistics, Series 10, No. 145. DHHS Pub. No. (PHS) 84-1573 (1984).

Sweeney, D.F., et al. A synthetic polymer as a corneal onlay. Invest Ophthalmol Vis Sci; 40(4): S638 (1999). [ARVO abstract 3361].

Tham, V.M.B., et al. Microkeratome complications of laser in situ keratomileusis. Ophthalmology; 107: 920-24 (2000).

Thompson, K.P., et al. Current status of synthetic epikeratoplasty. Refract Corneal Surg.; May-June, 7(3): 240-8 (1991).

Thompson, K.P., et al. Synthetic epikeratoplasty in rhesus monkeys with human type IV collagen. Cornea; Jan; 12(1): 35-45 (1993).

Trinkaus-Randall, V. et al. Implantation of a synthetic cornea: design, development, and biological response. Artif Organs.; 21: 1185-91 (1997).

Urry, D.W., et al. Elastic protein-based polymers in soft tissue augmentation and generation. J Biomater Sci.; Polymer Ed.; vol. 9, No. 10: 1015-48 (1998).

Van Hest, J.C., et al. Protein-based materials, toward a new level of structural control. Chern Commun (Camb); (19): 1897-904 (Oct. 7, 2001).

International Search Report for PCT/US2005/001773 filed on Jan. 21, 2005 in the name of David Tirrell, et al.

Written Opinion for PCT/US2005/001773 filed on Jan. 21, 2005 in the name of David Tirrell, et al.

International Preliminary Report on Patentability for PCT/US2005/001773 filed on Jan. 21, 2005 in the name of David Tirrell, et al.

Supplementary European Search Report for EP05711698.0 filed on Jan. 21, 2005, in the name of the California Institute of Technology, et al.

Heilshorn, S.C., DiZio, K.A., Welsh, E.R. and Tirrell, D.A. Endothelial cell adhesion to the fibronectin CS5 domain in artificial extracellular matrix proteins. Biomaterials, vol. 24, No. 23: 4245-4252 (2003).

Yao, J. and Asakura, T. Synthesis and Structural Characterization of Silk-Like Materials Incorporated with an Elastic Motif. J. Biochem. vol. 133, No. 1: 147-154 (2003).

Goldfischer, S. Coltoff-Schiller, B. and Goldfischer M. Microfibrils, Elastic Anchoring Components of the Extracellular Matrix, are associated with Fibronectin in the Zonule of Zinn and Aorta. Tissue & Cell, vol. 17, No. 4; 441-450 (1985).

Non-Final Office Action issued by the USPTO for U.S. Appl. No. 11/040,130 dated Jan. 13, 2006.

Non-Final Office Action Office Action issued by the USPTO for U.S. Appl. No. 11/040,130 dated Jul. 14, 2005.

Final Office Action issued by the USPTO for U.S. Appl. No. 11/040,130 dated Sep. 25, 2006.

Notice of Allowance issued by the USPTO for U.S. Appl. No. 11/040,130 Feb. 7, 2007.

Office Communication 94(3) issued by the European Patent Office for European Application No. EP05711698.0 dated Mar. 12, 2010.

Office Action issued by the JPO for JP Application No. 2006-551255 dated Nov. 10, 2010.

* cited by examiner

Histology: Controls (Sham Surgery)

ENGINEERED PROTEINS, AND METHODS OF MAKING AND USING

CROSS-REFERENCE TO RELATED APPLICATIONS

This application claims the benefit under 35 U.S.C. 119(e) of U.S. Provisional Application No. 60/538,844, which was filed Jan. 23, 2004, and U.S. Provisional Application No. 60/552,029, which was filed Mar. 10, 2004, which are both hereby incorporated by reference in their entireties. This application further claims priority under 35 U.S.C. 120 as a continuation of U.S. patent application Ser. No. 11/040,130 "Engineered proteins, and methods of making and using" filed Jan. 21, 2005, which is hereby incorporated by reference in its entirety.

STATEMENT REGARDING FEDERALLY SPONSORED RESEARCH OR DEVELOPMENT

The present invention was developed with funds from the United States Government, National Institutes of Health grant number R01-HL59987 and National Science Foundation Grant No. BES-9901648. Therefore, the United States Government has certain rights in the invention.

TECHNICAL FIELD

The present invention pertains to engineered proteins, especially when used to make biomedical moldings such as ophthalmic moldings.

BACKGROUND OF THE INVENTION

The cornea accounts for two-thirds of the refractive power of the human eye. This power can be altered by changing the corneal curvature or by varying the cornea's index of refraction. According to the National Center for Health Statistics, approximately 52% of the United States population wears some form of corrective lenses. While there have been significant advancements over the past decade in refractive surgery to correct myopia, hyperopia, and astigmatism, certain problems remain. Laser in situ keratomileusis (LASIK) and photorefractive keratectomy (PRK) have proven very effective in the correction of myopia, astigmatism, and low-moderate hyperopia. Principle limitations of these procedures are their lack of reversibility and limited efficacy in the correction of hyperopia and high myopia.

Recently, with FDA approval of a phakic intraocular lens (IOL) [Verisyse, Advanced Medical Optics Santa Ana, Calif.], there is a potentially improved means to treat high myopia. While these phakic IOLs provide excellent quality of vision to implanted myopes, they can be associated with severe intraocular complications such as endophthalmitis and corneal decompensation. Additionally, these IOLs are not as safe to implant in patients with hyperopia who tend to have shallow anterior chambers and are at increased risk for corneal damage from the implant.

These problems with current refractive surgical approaches have renewed interest in intracorneal implants (inlays) to treat hyperopia and high myopia. Implanting a lenticule in the cornea to correct refractive error is not a new idea. In 1949, Barraquer described implantation of 6 mm flint glass intracorneal lenses in a rabbit model. The corneas developed stromal necrosis and the lenses were extruded. Subsequent experiments by Barraquer using polymethylmethacrylate (PMMA) lenses had similar results. He concluded that limited metabolic exchanged across the synthetic onlay was incompatible with corneal viability. In 1967, Dohlman tested a hydrogel inlay made of glyceryl methacrylated in rabbits and cats. These water permeable implants enabled metabolic exchange and were better tolerated by the rabbit cornea; however, by 3 months, they were often extruded. In the cats there was excellent clinical biocompatibility and no extrusion. Other attempts at a synthetic inlay using colloidin, polypropylene, sialastic, and polysulfone were not well tolerated by the cornea, leading to loss of transparency.

Based on the initial promising results with hyrogel inlays, these materials have been the most exhaustively studied in animal models and more recently, in clinical trials. A microporous hydrogel formulation (Nutrapore®) has been incorporated in a corneal inlay (PermaVision®, Anamed Inc., Anaheim, Calif.) and implanted to correct hyperopia and high myopia. These inlays are 5.0 mm in diameter with a central thickness ranging from 25-60 µm. Their water content is 78% and the refractive index is similar to the cornea. Michieletto and co-workers reported on 10 hyperopes implanted with the PermaVision® lens using a microkeratome to create a corneal flap and securing the implant without sutures. While one inlay had to be removed due to decentration, no other eye lost best corrected visual acuity and the lenses appeared to be well tolerated for the 6 month follow up. Notably, no eye was operated that had more than 0.5 diopters of pre-operative astigmatism. Guell et al reported 6 hyperopic eyes implanted with a PermaVision® inlay. While all eyes were 20/40 or better at 12 months without correction, only 1 eye was 20/20 without correction. The authors concluded that predictability of inlay power "must be improved." Werblin and co-workers reported use of different hydrogel inlay, the Permalens® (Alcon Labs, Fort Worth, Tex.), to correct high myopia. Inlays ranging from −10.00 to −15.00 diopters were implanted in 5 myopic patients. With a follow up of at least 18 months in all cases, corneal clarity was maintained, but as in the hyperopic inlays, power predictability was a significant issue. In fact, the mean post-operative refractive error was −5.7±2.1 diopters. While these pilot studies using hydrogel inlays for correction of hyperopia and high myopia establish general biocompatibility (some studies have shown cases of perilenticular inflammation or fibrosis), they do reveal the need for adjustability to maximize visual outcomes. Because it is impossible to predict the post-operative refractive error in patients after implantation, a means to post-operatively adjust inlay power would be desirable.

A significant limitation of current hydrogel inlays is their inability to address the important need for post-operative adjustability.

U.S. Pat. No. 4,264,155 (issued to Miyata) discloses soft contact lenses made from collagen gels to which water-soluble organic polyhydroxy polymers, e.g., mucopolysaccharides, polyvinyl alcohols and the like are added, followed by chemical cross-linking of the gels. The polyhydroxy polymeric additives are said to "surround" the strands of the collagen molecules to protect them against microbial degradation. No teaching or suggestion is made in U.S. Pat. No. 4,264,155 of possibly acylating collagen to produce ethylenically unsaturated or polymeric substituted collagen which could then be polymerized to form useful biomedical articles having high biological and tissue acceptability.

It is known e.g. from WO 95/13764 to provide corneal prostheses composed of porous polymeric material for correcting the optical properties of an eye or altering the appearance thereof. Corneal inlays are in general implanted into or onto the cornea of a mammal using surgical methods, for example by making an incision in the stromal tissue of the cornea to form a pocket into which the onlay is placed, and then closing the incision by suturing.

An alternative approach to correction of refractive error is placement of a corneal onlay. This has the advantages of being reversible, surgically simpler, and stable. The idea is that placement of the onlay on the Bowman's layer over the corneal stroma changes the corneal curvature thereby altering the refractive power of the cornea.

One method involves removing the corneal epithelial cell layers of the cornea by scraping, placing a synthetic lenticule directly onto and in intimate contact with the corneal tissue and holding it in place for a period of time which is sufficient for the epithelial cells to recover, grow over the implant and thus fix it in a persistent manner. The initial temporary fixation of the onlay on the cornea is accomplished by the use of a biocompatible glue such as a commercially available collagen- or fibrin-based two components glue. However said glues have not yet proven satisfactory mainly because of severe handling problems.

In view of these and other drawbacks, there is a need for improved materials for biomedical moldings, and in particular, corneal onlays.

BRIEF SUMMARY OF THE INVENTION

The present invention provides an engineered protein and methods of making and using the engineered protein. The engineered protein of the present invention may be any non-naturally occurring protein, peptide, or polypeptide that, when cross-linked, may form a lens with favorable ophthalmic properties. In certain embodiments of the invention, the engineered protein comprises at least one fibronectin domain and at least one elastin domain. The protein may be synthesized according to methods known to one with skill in the art, and may be a recombinant protein or a fusion protein. The fibronectin domain, in certain embodiments, may comprise a CS1, CS5, or type III domain, or an RGD domain. In other specific embodiments, the elastin domain comprises one or a combination of the amino acid sequences VPGVG (SEQ ID NO:2), VPGKG (SEQ ID NO:3), VPGIG (SEQ ID NO:4), or a functional equivalent thereof.

In one embodiment, the engineered protein comprises SEQ ID NO:1 (LD-YAVTGRGDSPASSKPIA((VPGIG)$_2$VPGKG (VPGIG)$_2$)$_4$VP)$_3$. It is also contemplated that the protein may have certain tags, such as a His tag, in order to facilitate purification. One with skill in the art realizes that such tags may be cleaved or otherwise removed, and do not contribute to the material properties of the engineered protein. In one embodiment of the invention, the engineered protein is less than 30 kilodaltons, is less that 15 kildaltons, or is less than 10 kilodaltons.

The protein may be cross-linked according to the present invention. It is contemplated that the cross-linking may be chemical or ultraviolet cross-linking. In certain embodiments, the cross-linking occurs in such a manner as to leave behind a minimum of impurities in the cross-linked product. One with skill in the art realizes that the elastic properties of the engineered protein may be altered by the degree of cross-linking, and that a more rigid product may be formed by increased cross-linking. One with skill in the art also realizes that the increase in cross-linking may be accomplished by altering the design of the protein. For example, in certain embodiments of the invention, the engineered protein is cross-linked via lysine residues in the domain VPGKG (SEQ ID NO:3). Increasing the number of lysines available for cross-linking may alter the elastic properties of the protein. Thus, the protein in SEQ ID NO:1 may be altered by changing the number of VPGIG (SEQ ID NO:4) repeating blocks versus the number of VPGKG (SEQ ID NO:3) blocks. In certain embodiments, impurities in the cross-linked product can be removed by rinsing or chemical extraction.

In certain embodiments, the invention provides an engineered protein composition comprising strands of repeating blocks of fibronectin-like and elastin-like domains. It is contemplated that the engineered protein composition may also include a repeating block of fibroin, elastin, keratin, collagen or combinations of repeating units.

An embodiment of the present invention is a lens comprising an engineered protein, wherein the engineered protein is cross-linked. In a specific embodiment, the lens is a contact lens, corneal onlay, corneal inlay or intraocular lens. In another specific embodiment, the product forms corneal graft or corneal patch. The engineered protein products of the present invention are suitable for corneal replacements, wherein all, or a part, of the corneal tissue is replaced with the engineered proteins described herein.

It is contemplated, in certain embodiments, that the lens is biocompatible, optically transparent, resistant to biodegradation, stimulates the adhesion of adjacent cells, and has favorable elastic properties. In one embodiment of the invention, the lens has an elastic modulus of about 0.01 to about 5.0 Mpa. In another embodiment, the lens has an elastic modulus of about 0.05 to about 2.0 Mpa. In another embodiment, the lens is substantially free of endotoxin or other contaminants.

Another embodiment of the invention is a film or coating made from the engineered proteins described herein.

Another embodiment of the invention is a method for correcting the optical properties of an eye by implanting into or onto the cornea a corneal onlay comprising an engineered protein, wherein the protein comprises at least one fibronectin domain and at least one elastin domain.

It is contemplated, in certain embodiments, that an adjustable biomedical implant, for example a corneal implant, can be prepared from the engineered protein by including reactive side chains that are susceptible to photochemical cross-linking. For example, an acryloyl or methacryloyl group may be attached to a lysine side chains of the protein of the present invention. One with skill in the art realizes that the number of amino acid residues in a single engineered protein that have acryloyl or methacryloyl may be adjusted. In certain embodiments of the invention, each engineered protein has at least one modified lysine residue with an acryloyl or methacryloyl group. In other embodiments of the invention, some lysine residues are modified, while others are unmodified. One with skill in the art realizes that changing the number of modified lysine residues yields photocurable variants that have variable material properties. One with skill in the art realizes that other amino acid residues may be similarly modified with reactive side chain that increase the degree of cross-linking. One with skill in the art is aware of techniques in which ophthalmic lenses may be adjusted. See for example, U.S. Patent Publication Nos. 20030176521 and 20030174375, both of the specifications of which are incorporated by reference herein.

In certain embodiments of the invention, the engineered protein is a low molecular weight protein that provides a basis for changing the local curvature of the implant through patterned irradiation and diffusion of low molecular weight species in response to an osmotic gradient. After the intended shape change is accomplished, the structure is "locked" by further irradiation of the entire implant.

In certain embodiments of invention, the engineered proteins of the present invention are contacted with small molecules that may diffuse through an engineered protein solution and aid the cross-linking or polymerization process.

In certain embodiments of the invention, the engineered proteins of the present invention may form a graft for the replacement for all or part of a cornea.

The foregoing has outlined rather broadly the features and technical advantages of the present invention in order that the detailed description of the invention that follows may be better understood. Additional features and advantages of the invention will be described hereinafter. It should be appreciated that the conception and specific embodiment disclosed may be readily utilized as a basis for modifying or designing other structures for carrying out the same purposes of the present invention. It should also be realized that such equivalent constructions do not depart from the invention as set forth herein. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

26. The Present Invention

Figure 1:
FIG. 1. shows the protein design for the engineered protein material. The full amino acid sequence is shown (SEQ ID NO:1). The fibronectin-derived domain (to promote interaction with the epithelial cells) and the elastin domain (for structural support flexibility) are shown. There is also a tag for protein identification, for protein purification, and a cleavage site.
Figure 2:
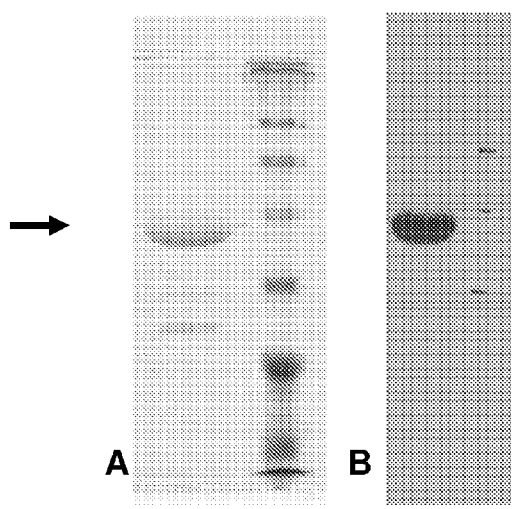
FIG. 2 shows an SDS gel and the corresponding Western blot showing the single band that represents the artificial protein which has a molecular weight of 35.1 kDa.
Figure 3:
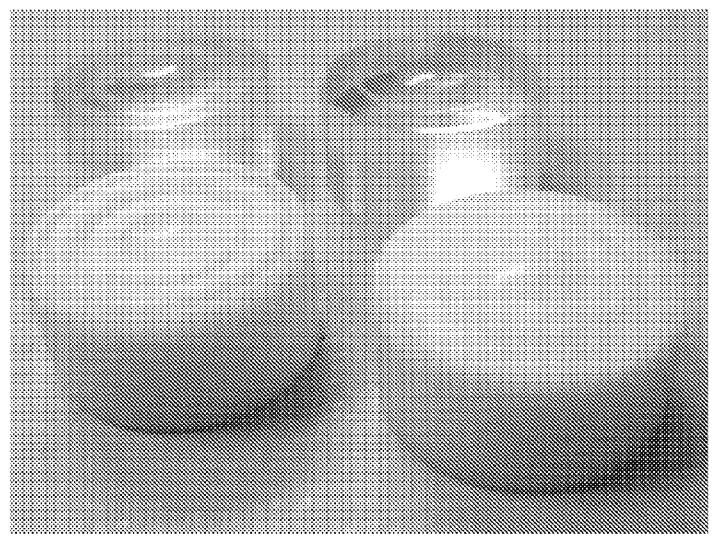
FIG. 3 shows how the engineered protein is cross-linked into onlays. The solution of engineered proteins then underwent a cross-linking reaction after having been molded into corneal onlays. The molds are shown. They are made of PMMA material to create a 6.0 mm onlay.
Figure 4:
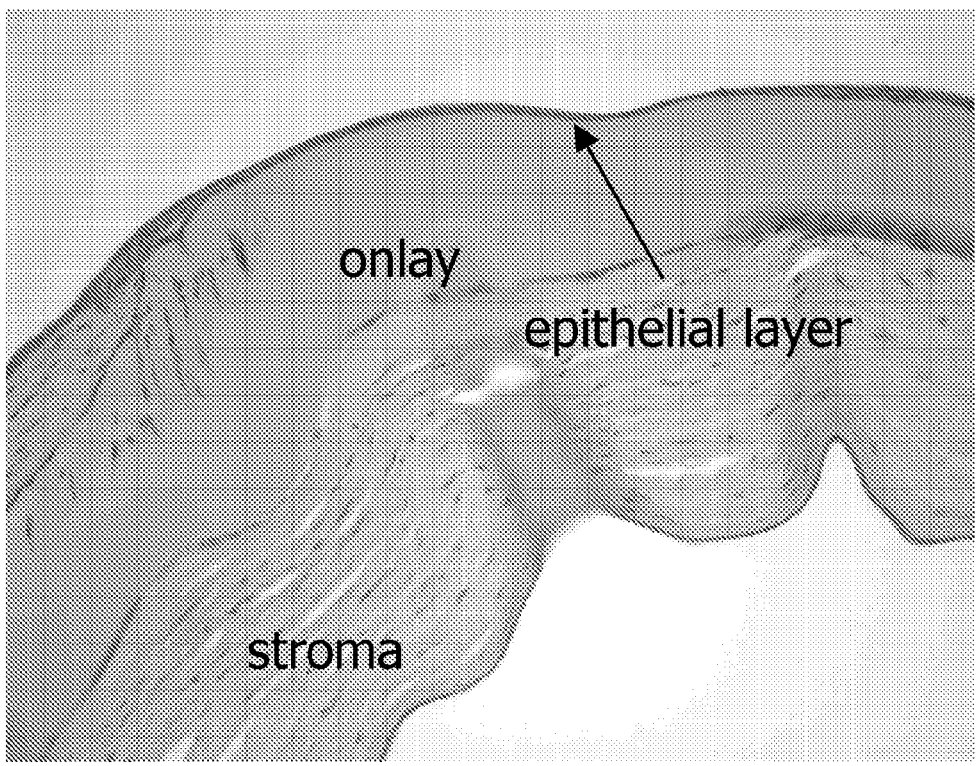
FIG. 4 shows an image of the onlay.

The present invention relates to an engineered protein product that can be formed into shaped articles useful in medical applications, including implants for ophthalmology, surgery, orthopedics and cardiology. These materials made from engineered proteins can also be used to replace part of or the entire cornea, i.e. as graft tissue following lamellar or penetrating keratoplasty. The engineered protein materials and products of the present invention may serve as both onlays and inlays. The engineered protein materials and products can be used in cataract surgery to replace the crystalline lens or as a phakic intraocular lens.

In certain embodiments of the invention, the lenses made from engineered proteins have at least one, and in certain embodiments all, of the following favorable ophthalmic properties: biocompatibility; predictable correction of myopia, hyperopia, and astigmatism; ability to correct high order aberrations, particularly spherical aberration, to confer vision better than 20/20; mechanical properties enabling ease of insertion and durability; ability to maintain stable refractive correction over time; ease and low cost manufacture; and, removability.

In preferred embodiments of the invention, the engineered protein product is a corneal onlay. The corneal onlay lenses contemplated by the present invention are constructed from de novo designed proteins, genetically engineered to include domains that provide favorable ophthalmic properties.

In certain embodiments of the invention, the engineered proteins are made from human fibronectin and mammalian elastin. The fibronectin domains, which may contain the amino acid sequence arginine-glycine-aspartic acid (RGD), are designed to facilitate cellular growth and adhesion. The elastin-like domains may make up the bulk of the protein, and are designed to ensure the elasticity of the cross-linked material. The application of engineered proteins as the basis for a corneal onlay has not been considered previously. These proteins have advantages for application in corneal onlays for the following reasons:

1) RGD sequences are known to promote adhesion to many cell types.
2) Elastin-like materials have previously been shown to be biocompatible.
3) Elastin, and elastin-like proteins, are generally resistant to enzymatic degradation, which extends their expected lifetime in the cornea.

4) Elastin-like proteins exhibit high molecular mobility in water, which is expected to promote good diffusion of nutrients through the onlay film.
5) The modular design of the protein means that only a few amino acid domains are present, while the biology of natural proteins that could be used in corneal onlays, such as collagen, is more complex.
6) The designed protein can be cross-linked using existing chemistry to produce transparent films, including corneal lens-shaped films.
7) The modulus of the cross-linked protein films is approximately 0.2 MPa, which is flexible enough for the application and sufficient to allow good surgical handling.

The corneal onlay as herein described, is capable of being surgically associated with, and preferably attached to, a living cornea so as to change its optical properties (such as correct vision deficiencies of the eye) or to change the appearance of the eye, such as coloration of the pupil. The onlay or a portion thereof may be colored with one or more pigments or dyes as are well known in the field. Colored onlays, and particularly coloration around the pupil area, will result in change of eye coloration on implantation.

The invention also contemplates numerous other uses for the engineered protein polymer compositions. Uses include, but are not limited to the following: manufacture of engineered tissue and organs, including structures such as patches, plugs or tissues of engineered protein material. These and other constructs can be supplemented with cells or used without cellular supplementation. Additional uses include the following: prosthetics, and other implants; tissue scaffolding, induction of differentiation of cells either in vitro or in vivo; repair or dressing of wounds; hemostatic devices; devices or structures for use in tissue repair and support such as sutures, adhesives, surgical and orthopedic screws, and surgical and orthopedic plates; natural coatings or components for synthetic implants; cosmetic implants and supports; repair or structural support for organs or tissues; substance delivery; bioengineering platforms; platforms for testing the effect of substances upon cells; cell culture; and numerous other uses.

27. Definitions

As used herein, the use of the word "a" or "an" when used in conjunction with the term "comprising" in the sentences and/or the specification may mean "one," but it is also consistent with the meaning of "one or more," "at least one," and "one or more than one." As used herein "another" may mean at least a second or more. Still further, the terms "having", "including", "containing" and "comprising" are interchangeable and one of skill in the art is cognizant that these terms are open ended terms.

As used herein, the term "cDNA" can refer to a single-stranded or double-stranded DNA molecule. For a single-stranded cDNA molecule, the DNA strand is complementary to the messenger RNA ("mRNA") transcribed from a gene. For a double-stranded cDNA molecule, one DNA strand is complementary to the mRNA and the other is complementary to the first DNA strand.

The term "conservative substitution" is used in reference to proteins or peptides to reflect amino acid substitutions that do not substantially alter the activity (specificity or binding affinity) of the molecule. Typically conservative amino acid substitutions involve substitution one amino acid for another amino acid with similar chemical properties (e.g. charge or hydrophobicity). The following six groups each contain amino acids that are typical conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). Internalizing peptides of the present invention may be modified to include conservative substitutions, so long as the substitutions do not affect the internalizing ability of the peptide.

As used herein, a "coding sequence" or a "nucleotide sequence encoding" a particular protein is a nucleic acid molecule which is transcribed and translated into a polypeptide in vivo or in vitro when placed under the control of appropriate regulatory sequences. The boundaries of the coding sequence are determined by a start codon at the 5'-terminus and a translation stop codon at the 3'-terminus. A coding sequence can include, but is not limited to, prokaryotic nucleic acid molecules, cDNA from eukaryotic mRNA, genomic DNA from eukaryotic (e.g. mammalian) sources, viral RNA or DNA, and even synthetic nucleotide molecules. A transcription termination sequence will usually be located 3' to the coding sequence.

As used herein, a protein "domain" refers to a functional unit of a peptide sequence. For example, VPGVG (SEQ ID NO:2) is an elastin domain. Additionally, the CS1 region of fibronectin is a domain. For the purposes of this invention, it is not necessary for a protein domain to have any particular structural or folding properties.

As used herein, the term "engineered protein" refers to a non-naturally-occurring polypeptide. The term encompasses, for example, a polypeptide that comprises one or more changes, including additions, deletions or substitutions, relative to a naturally occurring polypeptide, wherein such changes were introduced by recombinant DNA techniques. The term also encompasses a polypeptide that comprises an amino acid sequence generated by man, an artificial protein, a fusions protein, and a chimeric polypeptide. Those skilled in the art can readily generate engineered proteins useful according to this aspect of the invention. When several desired protein fragments or peptides are encoded in the nucleotide sequence incorporated into a vector, one of skill in the art will appreciate that the protein fragments or peptides may be separated by a spacer molecule such as, for example, a peptide, consisting of one or more amino acids. Generally, the spacer will have no specific biological activity other than to join the desired protein fragments or peptides together, or to preserve some minimum distance or other spatial relationship between them. However, the constituent amino acids of the spacer may be selected to influence some property of the molecule such as the folding, net charge, or hydrophobicity. Nucleotide sequences encoding for the production of residues which may be useful in purification of the expressed recombinant protein may be built into the vector. Such sequences are known in the art. For example, a nucleotide sequence encoding for a poly histidine sequence may be added to a vector to facilitate purification of the expressed recombinant protein on a nickel column. Once expressed, recombinant peptides, polypeptides and proteins can be purified according to standard procedures known to one of ordinary skill in the art, including ammonium sulfate precipitation, affinity columns, column chromatography, gel electrophoresis and the like. Substantially pure compositions of about 50 to 99% homogeneity are preferred, and 80 to 95% or greater homogeneity are most preferred for use as therapeutic agents. Engineered proteins may be produced by any means, including, for example, peptide, polypeptide, or protein synthesis.

As used herein, the term "gene" refers to a DNA molecule that either directly or indirectly encodes a nucleic acid or protein product that has a defined biological activity. One class of genes often encountered in the art is the so-called "reporter gene." A reporter gene is any gene whose expression is used as a measure of the activity of the control sequences to which it is operably linked. Examples of commonly used reporter genes include, but are not limited to, a beta-galactosidase gene, a chloramphenicol aminotransferase (CAT) gene, a luciferase (luc) gene, and genes encoding fluorescent proteins such as Green Fluorescent Protein (GFP), Blue Fluorescent Protein (BFP), etc. Ideally, reporter genes do not interfere with the underlying biological processes that are the target of the study. However, in some instances, it may be desirable to measure the activity of the control sequences by linking them to a gene whose product does alter the underlying biology of the system in which gene expression is occurring. Such genes, while also reporter genes, are often referred to as "biologically active" genes.

As used herein, the term "genomic DNA" refers to a DNA molecule from which an RNA molecule is transcribed. The RNA molecule is most often a messenger RNA (mRNA) molecule, which is ultimately translated into a protein that has a defined biological activity, but alternatively may be a transfer RNA (tRNA) or a ribosomal RNA (rRNA) molecule, which are mediators of the process of protein synthesis.

As used herein, two nucleic acid molecules are "functionally equivalent" when they share two or more quantifiable biological functions. For example, nucleic acid molecules of different primary sequence may encode identical polypeptides; such molecules, while distinct, are functionally equivalent. In this example, these molecules will also share a high degree of sequence homology. Similarly, nucleic acid molecules of different primary sequence may share activity as a promoter of RNA transcription, wherein said RNA transcription occurs in a specific subpopulation of cells, and responds to a unique group of regulatory substances; such nucleic acid molecules are also functionally equivalent.

As used herein, a "heterologous" region of a DNA construct is an identifiable segment of DNA within or attached to another DNA molecule that is not found in association with the other molecule in nature. An example of a heterologous coding sequence is a construct where the coding sequence itself is not found in nature (e.g. synthetic sequences having codons different from the native gene). Allelic variation or naturally occurring mutational events do not give rise to a heterologous region of DNA as used herein.

As used herein, two nucleic acid molecules are "homologous" when at least about 60% to 75% or preferably at least about 80% or most preferably at least about 90% of the nucleotides comprising the nucleic acid molecule are identical over a defined length of the molecule, as determined using standard sequence analysis software such as Vector NTI, GCG, or BLAST. DNA sequences that are homologous can be identified by hybridization under stringent conditions, as defined for the particular system. Defining appropriate hybridization conditions is within the skill of the art. See e.g. Current Protocols in Molecular Biology, Volume I. Ausubel et al., eds. John Wiley:New York N.Y., pp. 2.10.1-2.10.16, first published in 1989 but with annual updating, wherein maximum hybridization specificity for DNA samples immobilized on nitrocellulose filters may be achieved through the use of repeated washings in a solution comprising 0.1-2×SSC (15-30 mM NaCl, 1.5-3 mM sodium citrate, pH 7.0) and 0.1% SDS (sodium dodecylsulfate) at temperatures of 65-68° C. or greater. For DNA samples immobilized on nylon filters, a stringent hybridization washing solution may be comprised of 40 mM $NaPO_4$, pH 7.2, 1-2% SDS and 1 mM EDTA. Again, a washing temperature of at least 65-68° C. is recommended, but the optimal temperature required for a truly stringent wash will depend on the length of the nucleic acid probe, its GC content, the concentration of monovalent cations and the percentage of formamide, if any, that was contained in the hybridization solution (Current Protocols in Molecular Biology, Volume I. Ausubel et al., eds. John Wiley: New York N.Y., pp. 2.10.1-2.10.16. 1989 with annual updating).

As used herein, the term "nucleic acid molecule" includes both DNA and RNA and, unless otherwise specified, includes both double-stranded and single-stranded nucleic acids. Also included are molecules comprising both DNA and RNA, either DNA/RNA heteroduplexes, also known as DNA/RNA hybrids, or chimeric molecules containing both DNA and RNA in the same strand. Nucleic acid molecules of the invention may contain modified bases. The present invention provides for nucleic acid molecules in both the "sense" orientation (i.e. in the same orientation as the coding strand of the gene) and in the "antisense" orientation (i.e. in an orientation complementary to the coding strand of the gene).

As used herein, the term "operably linked" refers to an arrangement of nucleic acid molecules wherein the components so described are configured so as to perform their usual function.

The terms "polypeptide", "peptide", or "protein" are used herein to designate a linear series of amino acid residues connected one to the other by peptide bonds between the alpha-amino and carboxy groups of adjacent residues. The amino acid residues are preferably in the natural "L" isomeric form. However, residues in the "D" isomeric form can be substituted for any L-amino acid residue, as long as the desired functional property is retained by the polypeptide. In addition, the amino acids, in addition to the 20 "standard" amino acids, include modified and unusual amino acids. Furthermore, it should be noted that a dash at the beginning or end of an amino acid residue sequence indicates either a peptide bond to a further sequence of one or more amino acid residues or a covalent bond to a carboxyl or hydroxyl end group.

As used herein, exogenous DNA may be introduced into a cell by processes referred to as "transduction", "transfection," or "transformation." Transduction refers to the introduction of genetic material, either RNA or DNA, across the membrane of a eukaryotic cell via a vector derived from a virus. Transfection refers to the introduction of genetic material across the membrane of a eukaryotic cell by chemical means such as by calcium phosphate-mediated precipitation, by mechanical means such as electroporation, or by physical means such as bioballistic delivery. Transformation refers to the introduction of genetic material into noneukaryotic cells, such as bacterial cells or yeast cells, by chemical, mechanical, physical or biological means. The genetic material delivered into the cell may or may not be integrated (covalently linked) into chromosomal DNA.

28. The Corneal Epithelium

The cornea serves several important functions for vision, e.g., refracting >80% of the incoming light onto the retina, filtering out harmful UV rays, and maintaining an optical "window." The cornea is composed of five structural layers: the epithelium, Bowman's layer, stroma, Descemet's membrane, and endothelium. The outermost layer, the corneal epithelium, is a multi-layered structure with a complex arrangement of intercellular junctions, chemical signaling, and nerve endings. Similar to other epithelial layers throughout the body, the corneal epithelium prevents entry of pathogens, provides a barrier against fluid loss, and protects against abrasive wounding. The epithelium is separated from the external environment only by a layer of fluid, the tears.

The corneal epithelium is composed of three types of cells—the basal cells (1 layer), wing cells (1-3 layers), and squamous cells (3-4 layers)—which adhere to one another by tight cell junctions. The basal cells also form strong adhesion complexes with the underlying extracellular matrix and ultimately with Bowman's layer. Bowman's layer, the anterior-most layer of the corneal stroma, is an acellular zone consisting of collagen fibrils and associated proteoglycans which are densely woven in a random fashion into a felt-like matrix. Of the cells in the epithelium, only the basal cells have mitotic capabilities. Like all stratified epithelia in the body, the corneal epithelium is self-renewing; complete cellular turnover occurs every 5-7 days. Generally, after the basal cells undergo mitosis, the daughter cells begin to move outward toward terminal differentiation and eventual desquamation. See C. Hanna et al., "Cell production and migration in the epithelial layer of the cornea," Arch. Ophthalmol., vol. 64, pp. 536 (1960).

In certain embodiments of the invention, it is contemplated that ophthalmic engineered protein products of the present invention, including corneal onlays, intraocular lenses, or contact lenses, will demonstrate confluent growth of epithelial cells over the surface of the product. Additionally, in some embodiments of the invention, the engineered protein products will demonstrate resistance to degradation and resistance to rejection. In certain embodiments, an engineered protein comprises component that promotes nerve growth through the implant, such a functional fragment of a nerve growth factor. In certain embodiments, where appropriate, a surgical technique may be used to allow the onlays of the present invention to adhere to the corneal stroma by physical adhesion. In other embodiments, the corneal onlay to may adhere to the cornea by means of a bioadhesive glue, such as fibrin tissue glue. In certain embodiments, a surgical pocket or flap between the corneal epithelium and Bowman's layer may be created surgically, or in specific embodiments, through use of a laser. The lenses of the present invention may then be implanted under the flap or in the pocket, without the use of a bioadhesive. One with skill in the art is aware that slight design modifications may be necessary to modify the design of the engineered protein, or the shape of the engineered protein product, to promote certain advantages, such as enhancing adhesion between the onlay and Bowman's Layer in the cornea.

29. Engineered Proteins

The engineered proteins of the present invention may be any protein that, when cross-linked or formed into a shaped product, has favorable ophthalmic properties, such as elasticity, transparency, biocompatability, etc. In certain embodiments of the invention, the engineered proteins are fusion proteins or chimeric proteins. In certain embodiments of the invention, the engineered proteins are made from a combination of human protein domains from various protein sources. In one embodiment of the invention, the engineered protein comprises at least one domain from a human extracellular matrix protein. In another embodiment of the invention, the human protein domain is a variant of the wild-type protein that has been modified to increase the favorable ophthalmic properties of the engineered protein.

One example of a domain or protein fragment suitable for use in an engineered protein is an elastin domain. Elastin (SEQ ID NO:29) is a structural molecule which offers great strength and flexibility. It is resistant to breakdown. Its sequence largely consists of simple repeating sequences of hydrophobic amino acids. An important feature of elastin which accounts for its unique structure and insolubility is its extensive cross-linking between polypeptide chains that occurs at lysine residues. One typical repeating sequence of elastin is VPGVG (SEQ ID NO:2). Fibronectin (SEQ ID NO:28) is a modular protein composed of homologous repeats of three prototypical types of domains known as types I, II, and III. Fibronectin type III (FN3) repeats are both the largest and the most common of the fibronectin subdomains. FN3 exhibits functional as well as structural modularity. Sites of interaction with other molecules have been mapped to short stretch of amino acids such as the Arg-Gly-Asp (RGD) sequence found in various FN3 domains. The RGD sequences is involved in interactions with integrin. Small peptides containing the RGD sequence can modulate a variety of cell adhesion invents associated with thrombosis, inflammation, and tumor metastasis. In the cornea, fibronectin is known to play an important role in wound healing: it triggers epithelial cells to grow, migrate and adhere to the underlying extracellular matrix. Some other proteins known to contain an FN3 domain are: Contactin 2 or axonin-1 protein, Collagen alpha 1 chain, Neural cell adhesion protein L1, Leukocyte common antigen, and Contactin protein.

Generally, blocks include groups of repeating amino acids making up a peptide sequence that occurs in a protein. Genetically engineered proteins are qualitatively distinguished from sequential polypeptides found in nature in that the length of their block repeats can be greater (up to several hundred amino acids versus less than ten for sequential polypeptides) and the sequence of their block repeats can be almost infinitely complex. Table 1 depicts examples of genetically engineered blocks. Table 1 and a further description of genetically engineered blocks may be found in Franco A. Ferrari and Joseph Cappello, Biosynthesis of Protein Polymers, in: Protein-Based Materials, (eds., Kevin McGrath and David Kaplan), Chapter 2, pp. 37-60, Birkhauser, Boston (1997). An engineered protein of the present invention may comprise any of the below sequences in any order, in any number of repeats, and in combination with any other suitable domain, such as a fibronectin domain or an elastin domain, to provide a protein that, when formed into a lens or artificial tissue, provides favorable ophthalmic properties. The engineered proteins of the present invention also include functional variants of any of the sequences described herein. In certain embodiments of the invention, a functional variant has at least 80% sequence homology to its reference sequence.

TABLE 1

Protein polymer sequences

| Polymer Name | | Monomer Amino Acid Sequence |
|---|---|---|
| SLP 3 | (SEQ ID NO:5) | [(GAGAGS)$_9$GAAGY)] |
| SLP 4 | (SEQ ID NO:6) | (GAGAGS)$_n$ |
| SLP F | (SEQ ID NO:7) | [(GAGAGS)$_9$ GAAVTGRGDSPASAAGY]$_n$ |
| SLP L3.0 | (SEQ ID NO:8) | [(GAGAGS)$_9$ GAAPGASIKVAVSAGPSAGY]$_n$ |
| SLP L3.1 | (SEQ ID NO:9) | [(GAGAGS)$_9$ GAAPGASIKVAVSGPSAGY]$_n$ |
| SLP F9 | (SEQ ID NO:10) | [(GAGAGS)$_9$ RYVVLPRPVCFEKAAGY]$_n$ |
| ELP I | (SEQ ID NO:11) | [(VPGVG)$_4$]$_n$ |
| SELP 0 | (SEQ ID NO:12) | [(GVGVP)$_8$(GAGAGS)$_2$]$_n$ |
| SELP 1 | (SEQ ID NO:13) | [GAA(VPGVG)$_4$VAAGY (GAGAGS)$_9$]$_n$ |
| SELP 2 | (SEQ ID NO:14) | [(GAGAGS)$_6$GAAGY(GAGAGS)$_8$ (GVGVP)$_8$]$_n$ |
| SELP 3 | (SEQ ID NO:15) | [(GVGVP)$_8$(GAGAGS$_8$)]$_n$ |
| SELP 4 | (SEQ ID NO:16) | [(GVGVP)$_{12}$(GAGAGS)$_8$]$_n$ |

TABLE 1-continued

Protein polymer sequences

| Polymer Name | | Monomer Amino Acid Sequence |
|---|---|---|
| SELP 5 | (SEQ ID NO:17) | [(GVGVP)$_{16}$(GAGAGS)$_8$]$_n$ |
| SELP 6 | (SEQ ID NO:18) | [(GVGVP)$_{32}$(GAGAGS)$_8$]$_n$ |
| SELP 7 | (SEQ ID NO:19) | [(GVGVP)$_8$(GAGAGS)$_6$]$_n$ |
| SELP 8 | (SEQ ID NO:20) | [(GVGVP)$_8$(GAGAGS)$_4$]$_n$ |
| KLP 1.2 | (SEQ ID NO:21) | [(AKLKLAEAKLELAE)$_4$]$_n$ |
| CLP 1 | (SEQ ID NO:22) | [GAP(GPP)$_4$]$_n$ |
| CLP 2 | (SEQ ID NO:23) | {[GAP(GPP)$_4$]$_2$GPAGPVGSP}$_n$ |
| CLP-CB | (SEQ ID NO:24) | {[GAP(GPP)$_4$]$_2$(GLPGPKGDRGDAGPKGADGSPGPA)GPAGPVGS-P}$_n$ |
| CLP 3 | (SEQ ID NO:25) | (GAPGAPGSQGAPGLQ)$_n$ |

Repetitive amino acid sequences of selected protein polymers. SLP=silk like protein; SLPF=SLP containing the RGD sequence from fibronectin; SLPL 3/0 and SLPL 3/1=SLP containing two difference sequences from laminin protein; ELP=elastin like protein; SELP=silk elastin like protein; CLP=collagen like protein; CLP-CB=CLP containing a cell binding domain from human collagen; KLP=keratin like protein.

Elastin-mimetic peptides are non-natural polymers having repeated amino acid segments. These repeated amino acid segments or block repeats are generally penta-peptide sequences of GXGXP (SEQ ID NO:35), where X is α or β with respect to GaGβP, and α and β are any natural amino acid or functional amino acid derivative or analogue. See Urry D W. Physical chemistry of biological free energy transduction as demonstrated by elastic protein-based polymers. J. Phys. Chem 1997; 101:11007, 11013-14. The specific amino acid composition of the penta-peptide has predictable consequences on various biophysical properties of an elastin-mimetic peptide. Ibid. at 11010-11015 (see in particular Tables 2 and 3, also reproduced below).

Figure 9:
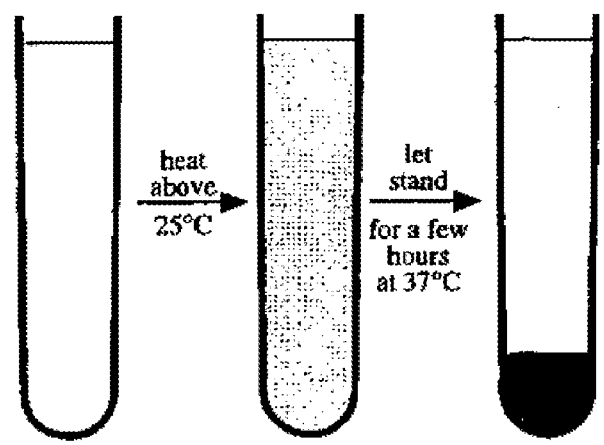
FIG. 9 shows the behavior of a binary mixture of elastin-mimetic peptide $(GVGVP)_{251}$ undergoing temperature dependent inverse phase transition from a transparent solution to an opaque gel. (Urry, "Physical Chemistry of Biological Free Energy Transduction As Demonstrated by Elastic Protein-Based Polymers," J. Phys. Chem. B., 101: 11007-11028, 1997, page 11012)

Elastin-mimetic peptides display a biophysical property termed "inverse phase transition." This inverse phase transition results in elastin-mimetic peptides changing conformation from a soluble form to an insoluble form as the temperature increases. Ibid. at 11011-11012. This inverse phase transition is thought to be the result of a hydrophobic folding phenomenon where water of hydration is excluded and the elastin-mimetic peptide changes to a more ordered structure. Ibid. at 11012. This inverse phase transition is experimentally measured by monitoring optical turbidity. See Urry D W. Physical chemistry of biological free energy transduction as demonstrated by elastic protein-based polymers. J. Phys. Chem 1997; 101:11007, 11012—FIG. 1. It is a common property of elastin-mimetic peptides to form optically clear solutions below the LCST and turbid solutions above the LCST. Ibid. at 11011 to 11012. These turbid solutions separate into an opaque, viscoelastic phase if maintained above the LCST. Ibid.; See FIG. 9.

The folding process occurs intrinsically and independently within each penta-peptide segment of an elastin-mimetic peptide. See Van Hest J C, Tirrell D A. Protein-based materials, toward a new level of structural control. Chem Commun (Camb). 2001 Oct. 7; (19):1897, 1900-1901. The independent pentapeptide folding processes allow for the inclusion of other amino acid sequences interspersed among penta-peptide units without significant impact on the inverse phase transition behavior of the penta-peptide units. Ibid. at 1901; Urry D W, Pattanaik A. Elastic protein-based materials in tissue reconstruction. Ann N Y Acad Sci. 1997 Dec. 31; 831:32, 41-43.

As shown in Tables 2 and 3, varying the α and β position amino acids impacts the threshold temperature at which an elastin-mimetic experiences inverse phase transition. Based upon extensive experimental analysis, summarized in part by Tables 2 and 3, one can predictably modify the penta-peptide content to design an elastin-mimetic peptide with a desired inverse phase transition temperature. See Van Hest J C, Tirrell D A. Protein-based materials, toward a new level of structural control. Chem Commun (Camb). 2001 Oct. 7; (19):1897, 1900-1901.

Reproduced from Urry et al., "Elastic Protein-based Materials in Tissue Reconstruction," Bioartificial Organs Science, Medicine, and Technology, Prokop et al., eds., The New York Academy of Sciences, Vol. 831, pp. 32-46,1997, page 35.

TABLE 2

Reproduced from Urry et al., "Elastic Protein-based Materials in Tissue Reconstruction," Bioartificial Organs: Science, Medicine, and Technology, Prokop et al., eds., The New York Academy of Sciences, Vol. 831, pp. 32-46, 1997, page 35.

| Residue X | | $T_{t3}$ Linearly Extrapolated to $Fx = 1$ | Correlation Coefficient |
|---|---|---|---|
| Lys (dihydro NMeN)$^a$ | | −130° C. | 1.0000 |
| Trp | (W) | −90° C. | 0.993 |
| Tyr | (Y) | −55° C. | 0.999 |
| Phe | (F) | −30° C. | 0.999 |
| His (imidazole) | (H°) | −10° C. | 1.000 |
| Pro | (P)$^b$ | (−8° C.) | Calculated |
| Leu | (L) | 5° C. | 0.999 |
| Ile | (I) | 10° C. | 0.999 |
| Lys (6-OH tetrahydro NMeN)$^a$ | | 15° C. | 1.000 |
| Met | (M) | 20° C. | 0.996 |
| Val | (V) | 24° C. | Reference |
| Glu (COOOCH$_3$) | (E$^m$) | 25° C. | 1.000 |
| Glu (COOH) | (E°) | 30° C. | 1.000 |
| Cys | (C) | 30° C. | 1.000 |
| His (imidazolium) | (H$^+$) | 30° C. | 1.000 |
| Lys (NH$_2$) | (K°) | 35° C. | 0.936 |
| Pro | (P)$^c$ | 40° C. | 0.950 |
| Asp (COOH) | (D°) | 45° C. | 0.994 |
| Ala | (A) | 45° C. | 0.997 |
| HyP | | 50° C. | 0.998 |
| Asn | (N) | 50° C. | 0.997 |
| Ser | (S) | 50° C. | 0.997 |
| Thr | (T) | 50° C. | 0.999 |
| Gly | (G) | 55° C | 0.999 |
| Arg | (R) | 60° C. | 1.000 |
| Gln | (Q) | 60° C. | 0.999 |
| Lys (NH$_3^+$) | (K$^+$) | 120° C. | 0.999 |
| Tyr (ø-O$^-$) | (Y$^-$) | 120° C. | 0.996 |
| Lys (NMeN, oxidized)$^a$ | | 120° C. | 1.000 |
| Asp (COO$^-$) | (D$^-$) | 170° C. | 0.999 |
| Glu (COO$^-$) | (E$^-$) | 250° C. | 1.000 |
| Ser (PO$_4^-$) | | 1000° C. | 1.000 |

$T_t$ - Based Hydrophobicity sacle for Proteins, $T_t$ = Temperature of Inverse Temperature Transition for poly[f$_v$(VPGVG (SEQ ID NO:2)), f$_x$(VPGXG (SEQ ID NO:30))]
$^a$NMeN is for N-methyl nicotinamide pendant on a lysyl side chain, i.e., N-methyl-nicotinate attached by amide linkage to the ε-NH$_2$ of Lys and the most hydrophobic reduced state is N-methyl-1,6-dihydronicotinamide (dihydro NMeN), and the second reduced state is N-methyl-6-OH, 1,4,5,6-tetrahydronicotinamide (6-OH tetrahydro NMeN).
$^b$The calculated $T_t$ value for Pro comes form poly (VPGVG) (SEQ ID NO:2) when the experimental values of Val and Gly are used. This hydrophobicity value of −8° C. is unique to the β-spiral structure where there is hydrophobic contact between the Val$^1$ γCH$_3$ and the adjacent Pro$^2_i$ δCH$_2$ and the interturn Pro$^2_{i+3}$βCH$_2$ moities.
$^c$The experimental value determined form poly[f$_x$(VPGVG (SEQ ID NO:2)), f$_p$(PPGVG) (SEQ ID NO:31)].

Reproduced from Urry, "Physical Chemistry of Biological Free Energy Transduction As Demonstrated by Elastic Protein-Based Polymers," J. Phys. Chem. B., 101:11007-11028, 1997, page 11011.

TABLE 3

| Residue | R Group | Abbreviation | Letter | $T_t{}^a$ | $\Delta H_t$ kcal/mol$^d$ ± 0.05 | $\Delta S_t$ kcal/mol$^d$ ± 0.05 |
|---|---|---|---|---|---|---|
| Tryptophan | 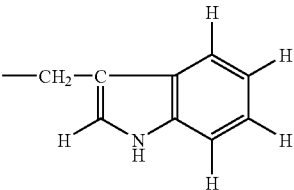 | Trp | W | −90° C. | 2.10 | 7.37 |
| Tyrosine | 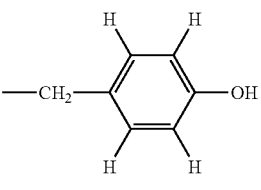 | Tyr | Y | −55° C. | 1.87 | 6.32 |
| Phenylalanine | 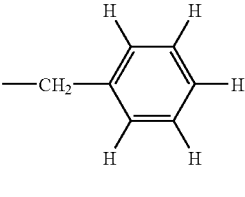 | Phe | F | −30° C. | 1.93 | 6.61 |
| Histidine | 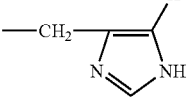 | His | H | −10° C. | | |
| Proline (calc.)$^b$ | —CH$_2$CH$_2$CH$_2$— | Pro | P | (−8° C.) | | |
| Leucine | —CH$_2$CH(CH$_3$)$_2$ | Leu | L | 5° C. | 1.51 | 5.03 |
| Isoleucine | —CH(CH$_3$)CH$_2$CH$_3$ | Ile | I | 10° C. | 1.43 | 4.60 |
| Methionine | —CH$_2$CH$_2$SCH$_3$ | Met | M | 20° C. | 1.00 | 3.29 |
| Valine | —CH(CH$_3$)$_2$ | Val | V | 24° C. | 1.20 | 3.90 |
| Histidine | 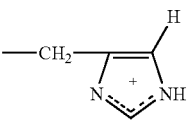 | His$^+$ | H$^+$ | 30° C. | | |
| Glutamic Acid | —CH$_2$CH$_2$COOH | Glu | E | 30° C. | 0.96 | 3.14 |
| Cysteine | —CH$_2$SH | Cys | C | 30° C. | | |
| Lysine | —CH$_2$CH$_2$CH$_2$CH$_2$NH$_2$ | Lys$^o$ | K$^o$ | 35° C. | 0.71 | 2.26 |
| Proline (exptl)$^c$ | —CH$_2$CH$_2$CH$_2$— | Pro | P | 40° C. | 0.92 | 2.98 |
| Alanine | —CH$_3$ | Ala | A | 45° C. | 0.85 | 2.64 |
| Aspartic Acid | —CH$_2$COOH | Asp | D | 45° C. | 0.78 | 2.57 |
| Threonine | —CH(OH)CH$_3$ | Thr | T | 50° C. | 0.82 | 2.60 |
| Asparagine | —CH$_2$CONH$_2$ | Asn | N | 50° C. | 0.71 | 2.29 |
| Serine | —CH$_2$OH | Ser | S | 50° C. | 0.59 | 1.86 |
| Glycine | —H | Gly | G | 55° C. | 0.70 | 2.25 |
| Arginine | —CH$_2$CH$_2$CH$_2$NHC(NH)NH$_2$ | Arg | R | 60° C. | | |
| Glutamine | —CH$_2$CH$_2$CONH$_2$ | Gln | Q | 60° C. | 0.55 | 1.76 |
| Lysine | —CH$_2$CH$_2$CH$_2$CH$_2$NH$_3{}^+$ | Lys | K | 120° C. | | |
| Tyrosinate | 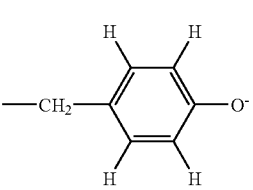 | Tyr$^-$ | Y$^-$ | 120° C. | 0.31 | 0.94 |

TABLE 3-continued

| Residue | R Group | Abbreviation | Letter | $T_t^a$ | $\Delta H_t$ kcal/mol$^d$ ± 0.05 | $\Delta S_t$ kcal/mol$^d$ ± 0.05 |
|---|---|---|---|---|---|---|
| Aspartate | —CH$_2$COO$^-$ | Asp$^-$ | D$^-$ | 120° C. | | |
| Glutamate | —CH$_2$CH$_2$COO$^-$ | Glu$^-$ | E$^-$ | 250° C. | | |

$^a$T$_t$ is the onset temperature for the hydrophobic folding and assembly transition, i.e., inverse temperature transition, in pbs(0.15 N NaCl, 0.01 M phosphate) as determined by light scattering. The values are linearly extrapolated to fx = 1 and rounded to a number divisible by 5. ΔH and ΔS are the values at fx = 0.2 on the curve for a linear fit of the DSC-derived endothermic heats and entropies of the transitions for the polymers in water.
$^b$The calculated T$_t$ value for Pro comes form poly(GVGVP (SEQ ID NO:32)) when the experimental values of Val and Gly are used. This hydropobicity value of −8° C. is unique to the β-spiral structure where there is hydrophobic contact between the Val$^1{}_i$ γ-CH$_3$ and adjecent Pro$^2{}_i$ δCH$_2$ and the interturn Pro$^2{}_{i+3}$ βCH$_2$ mioties.
$^c$The experimental value determined from poly [fv(GVGVP (SEQ ID NO:32))fp(GVGPP (SEQ ID NO:36))].
Per mole of pentamer.
Reproduced from Urry, "Physical Chemistry of Biological Free Energy Transduction As Demonstrated by Elastic Protein-Based Polymers," J. Phys. Chem. B., 101: 11007-11028, 1997, page 11011.
T$_t$ Based Hydrophobicity Scale for the Naturally Occurring Amino Acid Residues [in Order of More Hydrophobic (Low T$_t$) to More Polar (High T$_t$)$^e$ The working example molecule utilized below was designed based upon these known biophysical properties and parameters. The elastin-mimetic sequence III the working example is (((VPGIG)$_2$VPGKG(VPGIG)$_2$)$_4$VP)$_3$ (SEQ ID NO:34). In this example, Isoleucines occupy most of the a positions and Valines the B positions. Lysines at a minority of the a positions combine with the other amino acid content to yield both the desired inverse phase transition properties and amine groups for cross-linking peptides to form a matrix. See DiZio K, Tirrell D A. Mechanical properties of artificial protein matrices engineered for control of cell and tissue behavior. Macromolecules 2003; 36:1553, 1555-56.

Embodiments of the engineered protein include cross-linked protein products. The proteins may be cross-linked by reacting the proteins with a suitable and biocompatible cross-linking agent. Cross-linking agents include, but are not limited to glutaraldehyde, bis(sulfosuccinimidyl) suberate, p-Azidobenzolyl Hydazide, N-5-Azido-2-nitrobenzoyloxysuccinimide, 4-[p-Azidosalicylamido]butylamine-, any other suitable cross-linking agent and any combination thereof. A description and list of various cross-linking agents and a disclosure of methods of performing cross-linking steps with such agents may be found in the Pierce Endogen 2001-2002 Catalog which is hereby incorporated by reference. The engineered protein may be cross-linked by utilizing methods generally known in the art. For example, the engineered protein may be partially or entirely cross-linked by exposing, contacting and/or incubating the engineered protein device with a gaseous cross-linking reagent, liquid cross-linking reagent, light or combination thereof.

Figure 5:
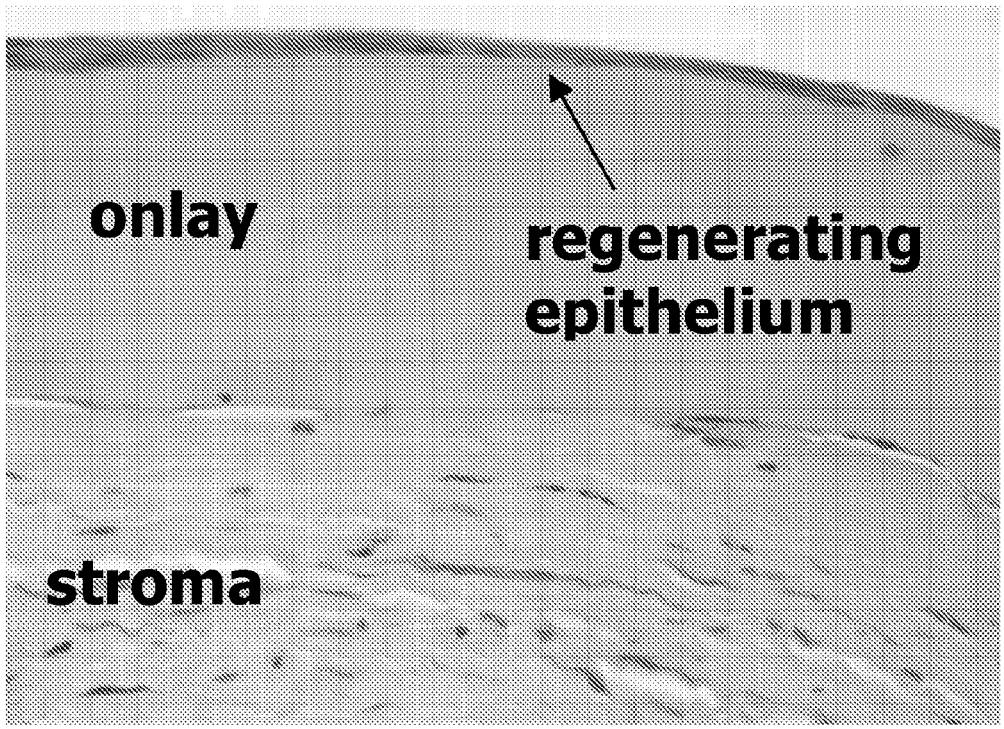
FIG. 5 shows clinical exam photos depicting the onlay implanted into the cornea immediately after the surgery, 48 hours after surgery, and one week after surgery. The open white arrows show the tucked-in edges of the implanted onlay within the pocket. The black arrows show the trephined wound. Fluorescein dye stains the entire exposed onlay surface. In the photo of the same eye 48 hours later, the reepithelialization process has begun and cells are migrating inward from the periphery, as evidenced by the lack of fluorescein dye in these areas. The black arrows show the edge of the initial wound for comparison. At one week after the surgery, the onlay has been incorporated and completely covered by epithelium. There is no fluorescein staining.
Figure 6:
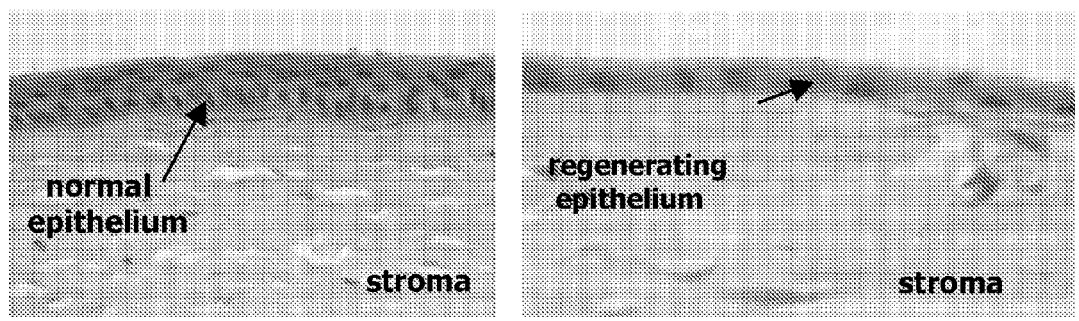
FIG. 6 shows a schematic section of the control eyes.
Figure 7:
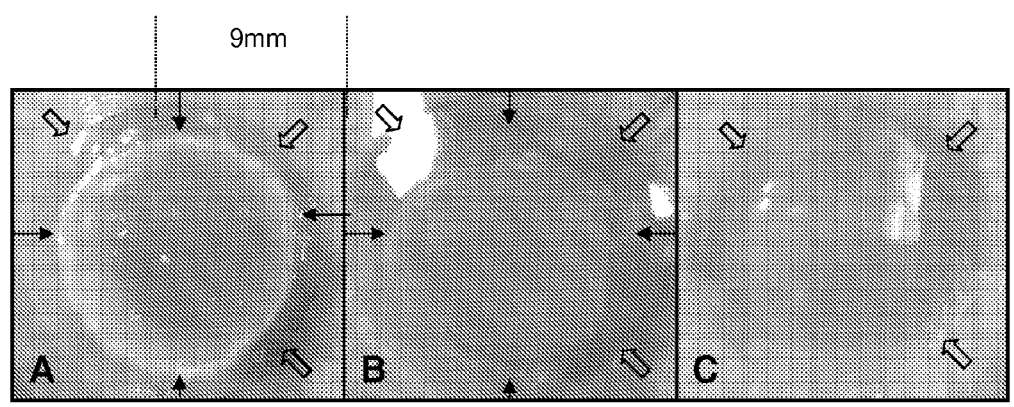
FIG. 7 shows a schematic section of the implanted onlays. A low-magnification view with PAS staining shows the onlay in the lamellar pocket. The distorted cornea structure is an artifact of the preservation process.
Figure 8:
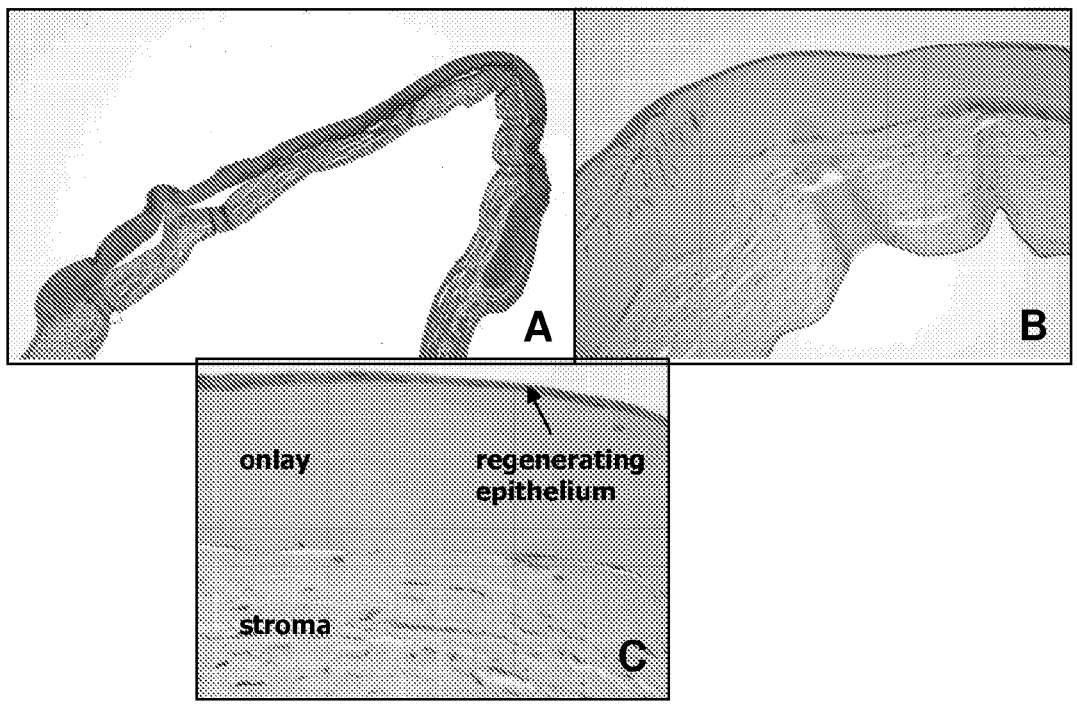
FIG. 8 shows histologic examination at the 7 day point. (A) At low magnification, Mason trichrome staining shows no staining of the novel onlay material compared to the natural cornea. (B) H & E stained specimens confirm reepithelialization of the onlay surface. (C) Higher magnification reveals the corneal stroma, the onlay, and the overlying epithelium to be 1-2 cell layers thick, typical for regenerating corneal epithelium.

One of skill in the art may select crosslinking techniques based on specific elastin-mimetic peptide sequences. The working example molecule contains Lysine residues which may be crosslinked to other Lysine residues using various known chemicals such as bis(sulfosuccinimidyl) suberate (BS3); disuccinimidyl suberate (DSS); or tris-succinimidyl aminotriacetate (TSAT). See DiZio K, Tirrell D A. Mechanical properties of artificial protein matrices engineered for control of cell and tissue behavior. Macromolecules 2003; 36:1553, e.g. FIG. 5; Trabbic-Carlson K, Setton L A, et al. Swelling and mechanical behaviors of chemically cross-linked hydrogels of elastin-like polypeptides. Biomacromolecules. 2003 May-June; 4(3):572, 574.

Other crosslinking techniques are compatible with the methods described herein. For example, an elastin-mimetic peptide lacking convenient reactive groups for crosslinking may easily be crosslinked by controlled gamma irradiation, generally in the amount of 20 Mrad. See Urry D W, Pattanaik A. Elastic protein-based materials in tissue reconstruction. Ann N Y Acad Sci. 1997 Dec. 31; 831:32, 40-41. See Urry D W. Physical chemistry of biological free energy transduction as demonstrated by elastic protein-based polymers. J. Phys. Chem 1997; 101:11007, 11014.

An adjustable biomedical implant, for example a corneal implant, can be prepared from the engineered protein by including reactive side chains that are susceptible to photochemical cross-linking. Attachment of acryloyl or methacryloyl groups to the lysine side chains of the protein yields photocurable variants that can be cross-linked by laser irradiation. Inclusion of low molecular weight proteins, similarly functionalized, provides a basis for changing the local curvature of the implant through patterned irradiation and diffusion of low molecular weight species in response to an osmotic gradient. After the intended shape change is accomplished, the structure is "locked" by further irradiation of the entire implant.

Engineered proteins of the present invention may also include therapeutic peptide fragments to provide therapeutic benefit to a patient when the proteins are used, for example, as lenses.

Peptide Synthesis

Engineered proteins of the present invention may be synthesized according to peptide synthesis techniques that are well known to those of skill in the art (Bodanszky et al., 1976) Peptide Synthesis, 1985; Solid Phase Peptide Synthelia, 1984); The Proteins, 1976. Appropriate protective groups for use in such syntheses will be found in the above texts, as well as in Protective Groups in Organic Chemistry, 1973. These synthetic methods involve the sequential addition of one or more amino acid residues or suitable protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group, such as lysine.

Using solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptides of the invention are preferably devoid of benzylated or methylbenzylated amino acids. Such protecting group moieties may be used in the course of synthesis, but they are removed before the peptides are used. Additional reactions may be necessary, as described elsewhere, to form intramolecular linkages to restrain conformation.

Fusion Proteins

The present invention relates to engineered proteins, which may be recombinant proteins. In certain embodiments of the invention, fusion proteins may be useful. Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and the second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., Gene 40:39-46, 1985; Murphy et al., Proc. Natl. Acad. Sci. USA 83:8258-8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

Protein Expression Systems

The engineered proteins of the present invention may be produced recombinantly. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

Other examples of expression systems include STRATAGENE®'s COMPLETE CONTROL™ Inducible Mammalian Expression System, which involves a synthetic ecdysone-inducible receptor, or its pET Expression System, an E. coli expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the Pichia methanolica Expression System, which is designed for high-level production of recombinant proteins in the methylotrophic yeast Pichia methanolica. One of skill in the art would know how to express a vector, such as an expression construct, to produce a nucleic acid sequence or its cognate polypeptide, protein, or peptide.

It is contemplated that the proteins, polypeptides or peptides produced by the methods of the invention may be "overexpressed", i.e., expressed in increased levels relative to its natural expression in cells. Such overexpression may be assessed by a variety of methods, including radio-labeling and/or protein purification. However, simple and direct methods are preferred, for example, those involving SDS/PAGE and protein staining or western blotting, followed by quantitative analyses, such as densitometric scanning of the resultant gel or blot. A specific increase in the level of the recombinant protein, polypeptide or peptide in comparison to the level in natural cells is indicative of overexpression, as is a relative abundance of the specific protein, polypeptides or peptides in relation to the other proteins produced by the host cell and, e.g., visible on a gel.

In some embodiments, the expressed proteinaceous sequence forms an inclusion body in the host cell, the host cells are lysed, for example, by disruption in a cell homogenizer, washed and/or centrifuged to separate the dense inclusion bodies and cell membranes from the soluble cell components. This centrifugation can be performed under conditions whereby the dense inclusion bodies are selectively enriched by incorporation of sugars, such as sucrose, into the buffer and centrifugation at a selective speed. Inclusion bodies may be solubilized in solutions containing high concentrations of urea (e.g. 8M) or chaotropic agents such as guanidine hydrochloride in the presence of reducing agents, such as β-mercaptoethanol or DTT (dithiothreitol), and refolded into a more desirable conformation, as would be known to one of ordinary skill in the art Proteinaceous Compositions In certain embodiments, the engineered proteins of the present invention may be a proteinaceous molecule. As used herein, a "proteinaceous molecule," "proteinaceous composition," "proteinaceous compound," "proteinaceous chain" or "proteinaceous material" generally refers, but is not limited to, a protein or polypeptide of at least two amino acids. All the "proteinaceous" terms described above may be used interchangeably herein. Additionally, the terms protein, peptide, and polypeptide may be used interchangeably herein.

In certain embodiments the size of the at least one proteinaceous molecule, or engineered protein, may comprise, but is not limited to, a molecule having about 2 to about 2500 or greater amino molecule residues, and any range derivable therein. The invention includes those lengths of contiguous amino acids of any sequence discussed herein.

As used herein, an "amino molecule" refers to any amino acid, amino acid derivative or amino acid mimic as would be known to one of ordinary skill in the art. In certain embodiments, the residues of the proteinaceous molecule are sequential, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties.

Accordingly, the term "proteinaceous composition" encompasses amino molecule sequences comprising at least one of the 20 common amino acids in naturally synthesized proteins, or at least one modified or unusual amino acid.

In certain embodiments the proteinaceous composition comprises at least one protein, polypeptide or peptide. In further embodiments the proteinaceous composition comprises a biocompatible protein, polypeptide or peptide. As used herein, the term "biocompatible" refers to a substance which produces no significant untoward effects when applied to, or administered to, a given organism according to the methods and amounts described herein. Such untoward or undesirable effects are those such as significant toxicity or adverse immunological reactions. In preferred embodiments, biocompatible protein, polypeptide or peptide containing compositions will generally be mammalian proteins or peptides or synthetic proteins or peptides each essentially free from toxins, pathogens and harmful immunogens.

Proteinaceous compositions may be made by any technique known to those of skill in the art, including the expression of proteins, polypeptides or peptides through standard molecular biological techniques, the isolation of proteinaceous compounds from natural sources, or the chemical synthesis of proteinaceous materials. The nucleotide and protein, polypeptide and peptide sequences for various genes have been previously disclosed, and may be found at computerized databases known to those of ordinary skill in the art. One such database is the National Center for Biotechnology Information's Genbank and GenPept databases. The coding regions for these known genes may be amplified and/or expressed using the techniques disclosed herein or as would be know to those of ordinary skill in the art. Alternatively, various commercial preparations of proteins, polypeptides and peptides are known to those of skill in the art.

In certain embodiments a proteinaceous compound may be purified. Generally, "purified" will refer to a specific or protein, polypeptide, or peptide composition that has been subjected to fractionation to remove various other proteins, polypeptides, or peptides, and which composition substantially retains its activity, as may be assessed, for example, by the protein assays, as would be known to one of ordinary skill in the art for the specific or desired protein, polypeptide or peptide.

It is contemplated that virtually any protein, polypeptide or peptide containing component may be used in the compositions and methods disclosed herein. However, it is preferred that the proteinaceous material is biocompatible. In certain embodiments, it is envisioned that the formation of a more viscous composition will be advantageous in that will allow the composition to be more precisely or easily applied to the tissue and to be maintained in contact with the tissue throughout the procedure. In such cases, the use of a peptide composition, or more preferably, a polypeptide or protein composition, is contemplated. Ranges of viscosity include, but are not limited to, about 40 to about 100 poise. In certain aspects, a viscosity of about 80 to about 100 poise is preferred.

Variants of Proteinaceous Compositions

Amino acid sequence variants of the proteins, polypeptides and peptides of the present invention can be substitutional, insertional or deletion variants. Deletion variants lack one or more residues of the native protein that are not essential for function or immunogenic activity. Another common type of deletion variant is one lacking secretory signal sequences or signal sequences directing a protein to bind to a particular part of a cell. Insertional mutants typically involve the addition of material at a non-terminal point in the polypeptide. This may include the insertion of an immunoreactive epitope or simply a single residue. Terminal additions, called fusion proteins, are discussed below.

Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The term "biologically functional equivalent" is well understood in the art and is further defined in detail herein. Accordingly, sequences that have between about 70% and about 80%; or more preferably, between about 81% and about 90%; or even more preferably, between about 91% and about 99%; of amino acids that are identical or functionally equivalent to the amino acids of the peptide mimetics provided the biological activity of the mimetic is maintained. (see Table 1, below for a list of functionally equivalent codons).

TABLE 4

Codon Table

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |

TABLE 4-continued

Codon Table

| Amino Acids | | | Codons | | | | | |
|---|---|---|---|---|---|---|---|---|
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and in its underlying DNA coding sequence, and nevertheless produce a protein with like properties. It is thus contemplated by the inventors that various changes may be made in the DNA sequences of genes without appreciable loss of their biological utility or activity, as discussed below.

In making such changes, the hydropathic index of amino acids may be considered. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine*−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still produce a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Cloning and Expression of aECM Protein "aE-RGD"

Protein aE-RGD with the amino acid sequence: M-MASMTGGQQMG-HHHHHH-DDDDK-(LD-YAVT-GRGDSPASSKPIA((VPGIG)$_2$VPGKG(VPGIG)$_2$)$_4$VP)$_3$-LE (SEQ ID NO:1) contains a T7 tag used for identification by western blotting, a 6-His tag that can be used for purification, an enterokinase cleavage site which allows the T7 and 6-His tags to be removed enzymatically, and three alternating repeats of the cell-binding elastin-like domains. The 17-amino acid cell-binding domain, which includes RGD, is taken from the tenth type III domain of fibronectin; it serves as a ligand for the $\alpha_v\beta_3$ and $\alpha_5\beta_1$ integrins. Other cell binding domains, including the CSI and CS5 domains from fibronectin, have also been genetically engineered into the same design, in place of the RGD domain. The cell-binding domain can be chosen, from these or other potential bioactive domains to elicit the most favorable cellular response. The elastin-like domains are modified versions of the (VPGVG (SEQ ID NO:2))$_x$ motif derived from mammalian elastin. Lysine residues are incorporated into the elastin-like domains to allow specific cross-linking through their nucleophilic side-chains. Other cross linking chemistries, including photocross-linking, can also be used.

Standard methods for cloning, bacterial growth, protein expression, sodium dodecyl sulfate-polyacrylamide gel electrophoresis (SDS-PAGE), and Western blotting were performed to produce aE-RGD. The gene for aE-RGD was placed under control of a T7 bacteriophage promoter in the pET28 expression vector and transformed into the protein expression host, BL21 (DE3)pLysS.

Host cells were grown in a 10 L fermenter (New Brunswick Scientific BioFlo 3000) using "terrific broth" media at pH 7.4. At an optical density of ~6, protein expression was induced with isopropyl-1-β-D-thiogalactosidase (IPTG); cells were harvested 1.5 hours after induction by centrifugation at 4° C.

Example 2

Purification of aE-RGD Protein

Cells containing the expressed aE-RGD protein were resuspended in TEN buffer (10 mM Tris-HCl, pH 7.5, 1 mM EDTA, 100 mM NaCl) at a concentration of 0.5 g/mL, and frozen at −20° C. The suspension was defrosted, lysing the cells, and shaken with 10 μg/mL of deoxyribonuclease I, 10 μg/mL of ribonuclease A, 5 mM magnesium chloride, and 1 mM phenylmethylsulfonyl fluoride to inhibit proteolysis, at 37° C. for 3 h, or at 4° C. overnight. The lower critical solution temperature (LCST) behavior of aE-RGD, where the protein separates from an aqueous solution as the temperature is raised, allows the protein to be purified by temperature cycling (the LCST of aE-RGD in water is 35° C.). The pH of the cell lysate was adjusted to 9.0, to ensure protein solubility, and centrifuged below the LCST (~1 h, 39,750 g, 4° C.). To the supernatant (containing the protein), 1 M NaCl was added, and centrifugation was repeated above the LCST (~1 h, 39,750 g, 37° C.). The pellet was redispersed in water to a concentration of 50-100 mg/mL. The temperature cycling was repeated twice; the purity of the protein (SDS-PAGE) increases each time.

The solution containing the aE-RGD protein was dialyzed at 4° C. for 3 days, to remove contaminants, and lyophilized. The purity and molecular weights of the proteins were verified by SDS-PAGE gels, Western blots, amino acid analysis, and matrix-assisted laser desorption ionization-mass spectrometry (MALDI-MS). Endotoxin levels can be reduced to accepted standards through similar purification protocols. Typical 10 L fermentations using these procedures have yielded 1 to 2 grams aE-RGD.

Example 3

Cross-linking aE-CS5 to Form Hydrogel Matrixes

Exemplary crosslinking experiments were performed using the above elastin-mimetic peptide having a CS5 domain in place of the RGD domain (aE-CS5). Two exemplary crosslinking protocols were applied. Protocol one employed bis(sulfosuccinimidyl) suberate (BS3) in PBS to crosslink peptide solution between two glass plates spaced 0.45 mm apart. Protocol two used an anhydrous dimethyl sulfoxide (DMSO) peptide solution and disuccinimidyl suberate (DSS) in anhydrous dimethylformamide (DMF). Table 5 summarizes various experimental details.

tested under simulated physiological conditions (PBS, pH 7.4, 37° C.) on an Instron Universal Testing Machine (Model 5564). A uniform strain rate of 10% gauge length per minute was used to test samples with an aspect ratio of at least 5 based on ASTM Sandard D 882-00. Sample dimensions were length 12±2 mm, width 2±1 mm, and thickness 0.45±0.1 mm. Samples are sandwiched between sheets of filter paper (in the region of the grips) and pressure-clamped in place. Typical elongations to break were 100-200%.

Cross-linking aE-CS5 with BS3 in PBS at 4° C. (well below the LCST) resulted in films with elastic moduli in the range of 0.08±0.01 to 0.19±0.01 MPa. These films remained transparent when subsequently allowed to reach physiological temperatures. Alternatively, crosslinking with DSS in a dimethylformamide solution yielded elastic moduli in the range of 0.30±0.06 to 0.97±0.31 MPa as shown in the following Table 6.

TABLE 6

Mechanical Properties of Cross-Linked Protein Films[a]

| Sample | no. of samples Tested | tensile Modulus E (MPa) | shear modulus G (MPa) |
|---|---|---|---|
| Method 1: Films Cross-Linked in PBS with BS3 | | | |
| 1 | 5 | 0.7 ± 0.03 | 0.022 ± 0.003 |
| 2 | 8 | 0.17 ± 0.01 | 0.055 ± 0.001 |
| 3 | 5 | 0.19 ± 0.01 | 0.060 ± 0.001 |
| 4 | 6 | 0.18 ± 0.02 | 0.060 ± 0.002 |
| 5 | 5 | 0.08 ± 0.01 | 0.026 ± 0.01 |
| Method II: Films Immersed in DMF/DSS Cross-Linking Solution | | | |
| 6 | 4 | 0.35 ± 0.31 | 0.12 ± 0.08 |
| 7 | 6 | 0.77 ± 0.12 | 0.25 ± 0.05 |
| 8 | 5 | 0.97 ± 0.31 | 0.32 ± 0.10 |
| elastin | | 0.30 ± 0.06 | |

[a]Sample numbers correspond to those in Table 5.

TABLE 5

Physical Properties of Cross-Linked Protein Films

| Sample | NHS/Lysine Stoichiometry | Protein Solution conc (w/v) | Reaction Temp (° C.) | Reaction Time (h) | Wt Fraction Protein | Reacted Lysines (%) | $M_c$ × 1000 (g/mol) |
|---|---|---|---|---|---|---|---|
| Method 1: Films Cross-Linked in PBS with BS3 | | | | | | | |
| 1 | 0.5:1 | 0.4 | 25 | >12 | 0.30 ± 0.03 | 42 ± 7 | 38 |
| 2 | 1:1 | 0.4 | 25 | >12 | 0.29 ± 0.02 | 75 ± 7 | 14 |
| 3 | 1.5:1 | 0.4 | 25 | >12 | 0.25 ± 0.03 | 76 ± 8 | 11 |
| 4 | 1:1 | 0.4 | 4 | >12 | 0.32 ± 0.02 | 74 ± 7 | 15 |
| 5 | 1:1 | 0.2 | 25 | >25 | 0.20 ± 0.02 | 61 ± 15 | 20 |
| Method II: Films Immersed in DMF/DSS Cross-Linking Solution | | | | | | | |
| 6 | 5:1 | dry film | 25 | >24 | 0.32 | | 7 |
| 7 | 10:1 | dry film | 25 | >24 | 0.37 ± 0.01 | | 4 |
| 8 | 100:1 | dry film | 25 | >24 | 0.39 ± 0.02 | 90 ± 7 | 2 |
| elastin | | | | | | | 6 |

[a] In films equilibrated at 37° C.

Example 4

Physical Properties of aE-CS5 Hydrogel Matrixes

Figure 10:
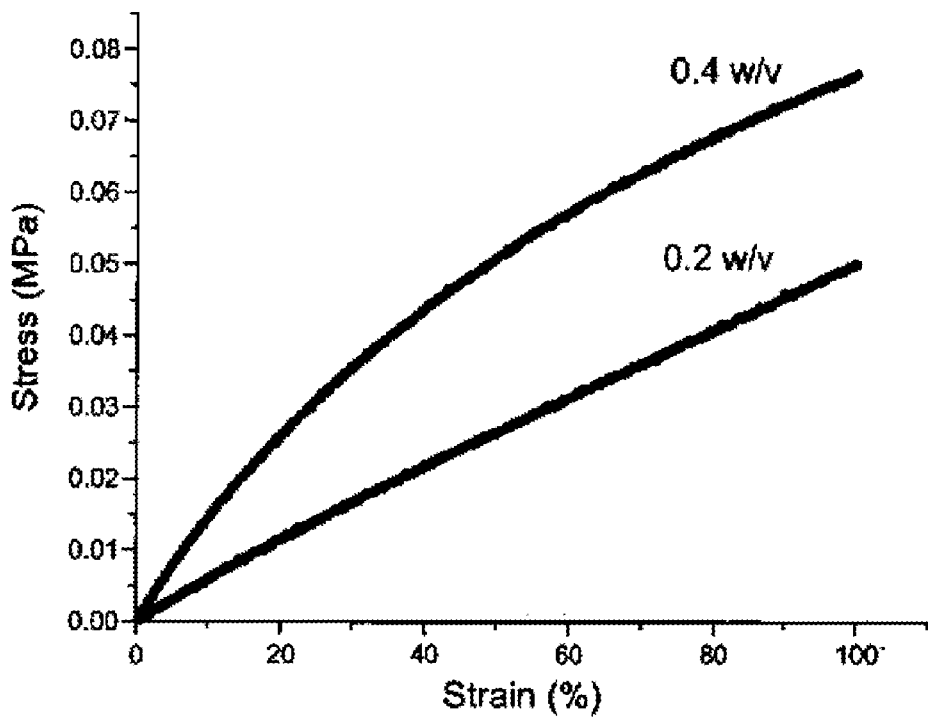
FIG. 10 shows Stress-strain behavior of films cross-linked at 0.4 and 0.2 w/v protein concentrations in PBS with BS3.

Tensile Testing: Protein films were measured after equilibration in BPS at 37° C. with vernier calipers and a micrometer to determine cross-sectional area. Samples were tensile For incompressible rubbers, the shear modulus (G) is one-third of the tensile modulus and can be related to the molecular weight between cross-links ($M_c$) through the relationship $$G = \rho RT \gamma M_c \quad (1)$$

Where ρ is the protein concentration in g/cm³, R is the gas constant, and T is the temperature. Equation 1 assumes the network is perfect, in that all chains are effective in giving rise to an elastic restoring force. The use of the protein concentration (ρ) to account for the reduction in the number of elastically effective chains in the hydrated film ignores any elastic effects of swelling. This assumption is appropriate for samples cross-linked in PBS but is likely to introduce some error into the estimation of $M_c$ for films cross-linked by immersion in DSS/DMF. FIG. 10 shows the tensile properties of films prepared by cross-linking solutions containing 0.2 and 0.4 w/v protein in PBS at 25° C. (Table 5, samples 2 and 5). The modulus of the sample prepared at higher concentration is approximately double that of the film prepared at 0.2 w/v protein, in accord with eq 1 (Table 6).

Figure 11:
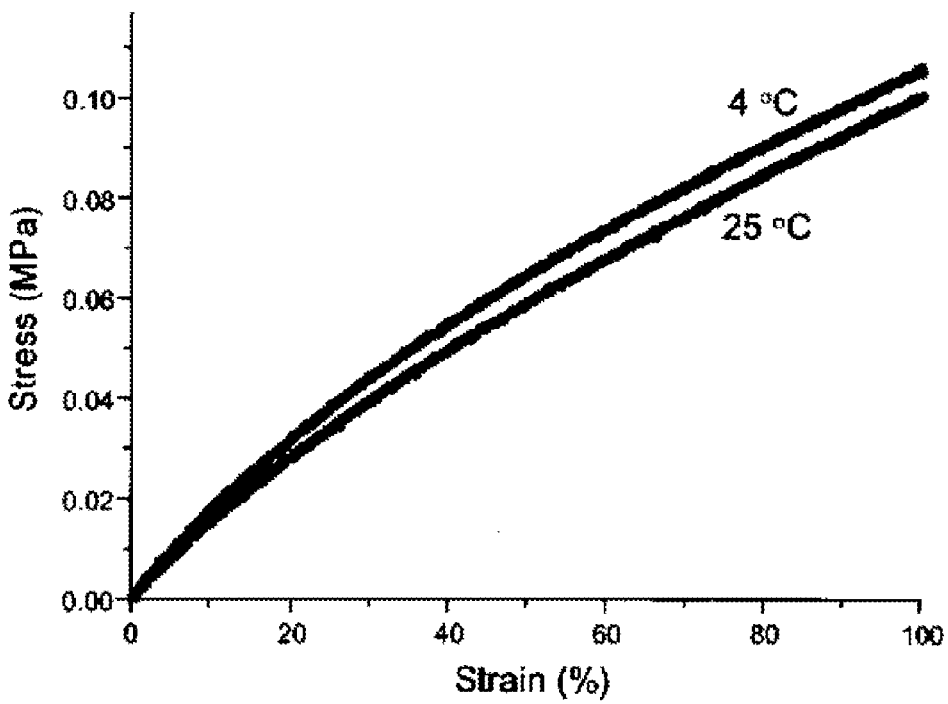
FIG. 11 shows Stress-strain behavior of films cross-linked above (25° C.) or below (4° C.) the LCST, showing little difference in mechanical properties.

Films cross-linked in PBS at 25° C. are white and opaque. In contrast, protein films cross-linked at 4° C. are clear and show no visible LCST transition on heating; i.e., they remain transparent at 37° C. FIG. 11 compares the tensile behavior of films cross-linked above and below the LCST. Although the samples differ strikingly in appearance, the modulus is unaffected when measured at 37° C. (Table 6).

Example 3

Cross-linking aE-RGD to Form Corneal Onlays

Cross-linking aE-RGD with bis(sulfosuccinimidyl) suberate (BS3) in water at 4° C. results in films with elastic modulus 0.2 MPa, which remain transparent at physiological temperatures. Corneal onlay lenses are made with this chemistry using two-piece PMMA molds of 6 mm optic diameter and 7.5 mm radius. All operations are done at 4° C., well below the LCST of aE-RGD, to ensure transparency. For each batch, 20 mg of aE-RGD is dissolved in 55 uL of water, then 2.3 mg of BS3 just dissolved in 20 uL of water is mixed in (the N-hydroxysuccinimidyl ester groups in BS3 are stoichiometric to primary-amines in the protein). The samples are quickly spun (10 sec) on a tabletop centrifuge to remove bubbles introduced in mixing. and 12 μL of the mixture is pipetted into each of 5 molds, which are assembled under a weight (~300 g) and cross-linked overnight at 4° C. Several lenses have been tested for elastic modulus, and a value of approximately 0.2 MPa is consistently seen. Contaminants and reaction byproducts are removed by exposing the lenses to excess water and ethanol, and the rinsed lenses are stored in a humidified container until use.

Example 4

Surgery

The rabbits used in the study (n=12) were anesthetized using inhaled 3% isoflurane and topical proparacaine. Throughout the surgery, the vital signs of the animals were carefully monitored including the corneal reflex, heart rate, respiration, and oxygen saturation. Initial attempts to adhere the corneal onlay were unsuccessful. The right eye of each animal was irrigated with betadine solution and a wire lid speculum was placed into the eye. An approximately 7 mm diameter area of the central corneal epithelium was removed by scraping. The corneal onlay was placed in the center of the abraded area. Blinking of the rabbit's eyelid dislodged the onlay. Tisseel® (Fibrinogen tissue sealant) was applied to the abraded cornea and the onlay was placed on the Tisseel®. The Tisseel® solidified to form a visible fibrin clot.

In order to securely adhere the onlay to the abraded cornea, a pocket in the cornea was created as described below. The right eye of each animal was irrigated with betadine solution and a wire lid speculum was placed into the eye. A 3.0 mm trephine was used to create a partial thickness keratotomy, approximately 100-200 microns in depth in the central cornea. The 0.12 forceps and the 69 blade were used to remove the stromal lamella within the trephined area from the base of the keratotomy. This left a circular keratectomy of 3.0 mm in diameter. A sharp pocket blade was used to make a 2 mm wide circular intralamellar pocket at the base of the keratotomy extending circumferentially outwards toward the corneal limbus.

Three groups of corneas were prepared. In group 1, (n=1) the wounds were created but no implants were placed. In group 2 (n=8), the same wounds were constructed and then the 5.0 mm diameter corneal onlay implant was carefully placed on the corneal surface. The implant was tucked 360 degrees into the grooved pocket using a blunt cyclodialysis spatula. No sutures were placed in this group. In group 3 (n=3), the same wound was constructed, the implants were placed in the pocket, and then 9-0 Nylon sutures were placed over the implant to keep it into place. After implantation, the eyes were irrigated with BSS solution. The rabbits were given an injection of Carprofen analgesic (5 mg/kg IM) postoperatively.

Example 5

Clinical Evaluation

Daily evaluation was performed for one week after implantation. The animals were closely followed for any signs of discomfort or wound infection. At any sign of discomfort, the animal was given one drop of topical 0.03% flurbiprofen and Carprofen 5 mg/kg IM q24 hours. The animals' weights were monitored. Slit lamp biomicroscopy was performed every 2-4 days following the initial procedure. Fluorescein staining with blue light was used to assess the re-epithelialization process. The speed and extent of re-epithelialization was noted as well as any signs of inflammation.

Example 6

Histology

Rabbits were euthanized using standard guidelines for large animals consisting of intramuscular Ketamine 35-50 mg/kg and Xylazine 5-10 mg/kg. Each animal also received an intracardiac injection of sodium pentobarbital and underwent bilateral thoracotomy. different time points.

The eyes were fixed in glutaraldehyde solution and examined histologically at different time points. The slides were stained with hematoxylin-eosin (H&E), periodic acid-Schiff (PAS), Mason tnchrome for collagen, and staining for mucopolysaccharides. Stained sections were mounted and viewed by light microscopy. The pattern of epithelial growth over the corneal implant was assessed histologically. The degree of inflammation both within the corneal stroma as well as within the implant was evaluated.

Light microscopy showed that epithelial cells had covered the entire implant of the cornea at the time of histologic examination one week after the surgery. The corneal epithelium overlying the implant was remarkably normal consisting of several cell layers. The interface between the corneal stroma and the implant was unremarkable. In a few cases, the corneal stroma and the corneal implant were notable for a moderate amount of inflammatory cells including lymphocytes and neutrophils. In other cases, the corneal stroma posterior to the implant and the corneal endothelium appeared normal and free of inflammation.

Example 7

Electron Microscopy

Several eyes were examined by electron microscopy. The animals were euthanized and the eyes were fixed as described for light microscopy. Several animals were used for electron microscopy to evaluate the implant and epithelial interface.

Example 8

Clinical Observations

The implants also tolerated the procedure well, as they were relatively easy to manipulate and durable during the surgery as long as they were well hydrated. All of the implants remained intact and well positioned within the circular stromal pocket. There was no difference in maintenance of the implant in the proper position whether sutures were placed or not. In the eyes where sutures were placed, the implants showed some surface wrinkling due to the tension that the sutures placed on the implant. Compared to the controls, initial mild to moderate inflammation was observed in all the eyes with the implants as shown by mild hyperemia of the bulbar conjunctiva and mild corneal stromal edema. There was no significant mucoid or purulent discharge noted in any of the animals.

Epithelialization in all cases initiated at the periphery of the exposed surface of the corneal onlays and progressed inward toward the center. The time required for full epithelialization varied somewhat between individual animals. All of the implant animals (groups 2 and 3) were partially re-epithelialized at the 96 hour time point, and all animals were fully re-epithelialized by the 1 week point. The control eyes in comparison were fully re-epithelialized by 96 hours. The animals tolerated the procedure well and there were no surgical complications.

Example 9

Epithelial Behavior

Normally, epithelial cells are anchored to the underlying basement membrane through adhesion complexes including hemidesmosomes and anchoring fibrils. Electron microscopy is used to look at the onlay-epithelial interface to look for formation of these structures in our long term studies. The next step will be to address the issue of adhesion to underlying Bowman's layer. The addition of a fibrinogen domain to the protein can facilitate adhesion in the presence of thrombin.

REFERENCES

All patents and publications mentioned in the specifications are indicative of the levels of those skilled in the art to which the invention pertains. All patents and publications are herein incorporated by reference to the same extent as if each individual publication was specifically and individually indicated to be incorporated by reference.
U.S. Pat. No. 4,264,155
U.S. Patent publication No. 2002/0028243
WO 95/13764

1) National Center for Health Statistics; Poe G S. Eye care visits and use of eyeglasses or contact lenses, United States, 1979 and 1980. Vital Health Statistics, 1984; 10:145.
2) Spectrum Consulting; Arons I. 2001. Obtained from the American Academy of Ophthalmology Web Site: www.aao.org
3) Carlson A N. LEO Clinical Topic Update: refractive surgery. Am Acad Ophthalmol 2001; 9-15.
4) Iskander N G, Peters N T, Penno E A, et al. Postoperative complications of laser in situ keratomileusis. Curr Opin Ophthalmol 2000; 11:273-279.
5) Tham V M B, Maloney R K. Microkeratome complications of laser in situ keratomileusis. Ophthalmology. 2000; 107; 920-924.
6) Kaufman H E, Barron B A, McDonald M B, Waltzman S R, eds. The Cornea. New York: Churchill Livingstone; 1988: 697-712.
7) Leibowitz H M, Trinkaus-Randall V, Tsuk A G, et al. Progress in the development of a synthetic cornea. Prog Retinal Eye Res 1994; 13:605-621.
8) Thompson K P, Hanna K, Waring G O 3rd, Gipson I, Liu Y, Gailitis R P, Johnson-Wint B, Green K. Current status of synthetic epikeratoplasty. Refract Corneal Surg. 1991 May-June; 7(3):240-8.
9) Sweeney D F, Xie R Z, O'Leary D J, et al. Nutritional requirements of the corneal epithelium and anterior stroma: Clinical findings. Invest Ophthalmol Sci 1998; 39:284-291.
10) Xie R Z, Stretton S, Sweeney D F. Artificial cornea: towards a synthetic onlay for correction of refractive error. Biosci Rep. 2001 August; 21(4):513-36.
11) McDonald M B. The future direction of refractive surgery. J Refract Surg 1988; 4:158-168.
12) Trinkaus-Randall V, Wu X Y, Tablante R, et al. Implantation of a synthetic cornea: design, development, and biological response. Artif Organs. 1997; 21:1185-1191.
13) Latkany R, Tsuk A, Sheu M S, et al. Plasma surface modification of artificial corneas for optimal epithelialization. J Biomed Mater Res 1997; 36:29-37.
14) Hicks C R, Chirila T V, Clayton A B, et al. Clinical results of implantation of the Chirila keratoprosthesis in rabbits. Br J Ophthalmol 1998; 82:18-25.
15) Legeais J M, Renard G. A second generation of artificial cornea (Biokpro II). Biomaterials 1998; 19:1517-1522.
16) Dupont D, Gravagna P, Albinet P, et al. Biocompatibility of human collagen type IV intracorneal implants. Cornea. 1989 December; 8(4):251-8.
17) Thompson K P, Hanna K D, Gipson I K, Gravagna P, Waring G O 3rd, Johnson-Wint B. Synthetic epikeratoplasty in rhesus monkeys with human type IV collagen. Cornea. 1993 January; 12(1):35-45.
18) Kornmehl E W, Bredvik B K, Kelman C D, et al. In vivo evaluation of collagen corneal allograft derived from rabbit dermis. J Refract Surg 1995; 11:502-506.
19) McCarey B E, Harrier C H, Rao P R. Collagen onlay epikeratoplasty after one year in the monkey model. Invest Ophthalmol Vis Sci 1997; 40(4); S511. [ARVO abstract 2362]
20) Lass J H, Stocker E G, Fritz M E, Collie D M. Epikeratoplasty. The surgical correction of aphakia, myopia, and keratoconus. Ophthalmology. 1987 August; 94(8):912-25.
21) Rao G N, Ganti S, Aquavella J V. Specular microscopy of corneal epithelium after epikeratophakia. Am J Ophthalmol. 1987 Mar. 15; 103(3 Pt 2):392-6.

22) Rodrigues M, Nirankari V, Rajagopalan S, et al. Clinical and histopathologic changes in the host cornea after epikeratophakia for keratoconus. Am J Ophthalmol 1992; 114: 161-70.
23) Xie R Z, Sweeney D F, Griesser H J, et al. A thin glycoprotein coating of a synthetic lenticule does not cause nutritional deficiency of the anterior cornea. Curr Eye Res 1999 May; 18(5):335-41.
24) Evans M D, Xie R Z, Tout S D, et al. Persistent adhesion of corneal epithelial tissue on synthetic lenticules in vivo. Aust N Z J Ophthalmol. 1998 May; 26 Suppl 1:S40-3.
25) Sweeney D F, Xie R Z, Tout S, et al. A synthetic polymer as a corneal onlay. Invest Ophthalmol Vis Sci 1999; 40(4): 5638. [ARVO abstract 3361]
26) Evans M D M, Xie R Z, Fabbri M, et al. Epithelialization of a synthetic polymer in the feline cornea: a preliminary study. Invest Ophthalmol Vis Sci 2000; 41:1674-1680.
27) Evans M D M, Xie R Z, Fabbri M, et al. Progress in the development of a synthetic corneal onlay. IOVS 2002; 43:3196-3201.
28) Chaouk H, Wilkie J S, Meijs G F, et al. New porous perfluropolyether membranes. J Appl Polym Sci 2001; 80:1756-1763.
29) Sweeney D F, Xie R Z, Evans M D, et al. A comparison of biologic coatings for the promotion of corneal epithelialization of synthetic surface in vivo. Invest Ophthalmol Vis Sci 2003; 44:3301-3309.
30) Van Hest J C, Tirrell D A. Protein-based materials, toward a new level of structural control. Chem Commun (Camb). 2001 Oct. 7; (19):1897-904.
31) Hong M, Isailovic D, McMillan R A, et al. Structure of an elastin-mimetic polypeptide by solid-state NMR chemical shift analysis. Biopolymers. 2003 October; 70(2):158-68.
32) Trabbic-Carlson K, Setton L A, et al. Swelling and mechanical behaviors of chemically cross-linked hydrogels of elastin-like polypeptides. Biomacromolecules. 2003 May-June; 4(3):572-80.
33) Urry D W, Pattanaik A, Xu J, et al. Elastic protein-based polymers in soft tissue augmentation and generation. J Biomater Sci Polym Ed. 1998; 9(10):1015-48.
34) Halstenberg S, Panitch A, Rizzi S, et al. Biologically engineered protein-graft-poly(ethylene glycol) hydrogels: a cell adhesive and plasmin-degradable biosynthetic material for tissue repair. Biomacromolecules. 2002 July-August; 3(4):710-23.
35) Liu J C, Heilshorn S C, Tirrell D A. Comparative cell response to artificial extracellular matrix proteins containing the RGD and CS5 cell binding domains. Biomacromolecules 2004 March-April; 5(2):497-504.
36) Johansson S, Svineng G, Wennerberg K, Armulik A, Lohikangas L. Fibronectin-integrin interactions. Front Biosci. 1997; 2:126-46.
37) Ruoslahti E, Pierschbacher M D. Arg-Gly-Asp: a versatile cell recognition signal. Cell. 1986; 44(4):517-8.
38) Giancotti F G, Ruoslahti E. Integrin signaling. Science 1999; 285(5430):1028-32.
39) Urry D W, Pattanaik A. Elastic protein-based materials in tissue reconstruction. Ann N Y Acad Sci. 1997 Dec. 31; 831:32-46.
40) Urry D W. Physical chemistry of biological free energy transduction as demonstrated by elastic protein-based polymers. J. Phys. Chem 1997; 101:11007-28.
41) Nicol A, Gowda D C, Urry D W. Cell adhesion and growth on synthetic elastomeric matrices containing Arg-Gly-Asp-Ser-3. J Biomed Mater Res. 1992 March; 26(3):393-413.
42) DiZio K, Tirrell D A. Mechanical properties of artificial protein matrices engineered for control of cell and tissue behavior. Macromolecules 2003; 36:1553-58.
43) Tisdale A S, Spun-Michaud S J, Rodrigues M et al. Development of the anchoring structures of the epithelium in rabbit and human fetal corneas. Invest Ophthalmol Vis Sci. 1988 May; 29(5):727-36.
44) Gipson I K, Spurr-Michaud S J, Tisdale A S. Hemidesmosomes and anchoring fibril collagen appear synchronously during development and wound healing. Dev Biol 1988; 126253-262.
45) Gipson I K, Spurr-Michaud S, Tisdale, et al. Reassembly of the anchoring structures of the corneal epithelium during wound repair in the rabbit. Invest Ophthalmol Vis Sci 1989; 30:425-434.
46) Jones J C R, Asmuth J, Baker S E, et al. Hemidesmosomes: extracellular matrix/intermediate filament connectors. Exp Cell Res 1994; 213:1-11.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A material for use in a mammalian eye, comprising: a crosslinked elastin-mimetic peptide polymer comprising pentapeptide repeats having the sequence GXGXP (SEQ ID NO:35), wherein X is any natural, modified, or unusual amino acid, wherein the material is in a shape compatible with incorporation into the eye, biocompatible, transparent to visible light, has a refractive index compatible with vision by the eye, the material is permeable to sufficient nutrients to maintain eye tissue integrity upon incorporation into an eye, and wherein the material forms a hydrogel in water and has an elastic modulus in the hydrogel state of about 0.01 MPa to about 5.0 MPa.

2. The material of claim 1, wherein the pentapeptide repeats are of an elastin domain.

3. The material of claim 2, wherein the elastin domain comprises a sequence selected from the group consisting of SEQ ID NO: 2-4, 11, 12-20, functional variants having at least 80% sequence identity to one of SEQ ID NO: 2-4, 11, 12-20 and combinations thereof.

4. The material of claim 1, 2 or 3 further comprising a sequence selected from the group consisting of SEQ ID NO: 21-23, 25 and combinations thereof.

5. A method of manufacturing a lens for incorporation into an eye, said method comprising the step of crosslinking an engineered polymer comprising pentapeptide repeats having the sequence GXGXP (SEQ ID NO: 35), wherein X is any natural, modified, or unusual amino acid, in a solution at a temperature below a lower critical solution temperature of the engineered polymer, thereby forming a hydrogel that is biocompatible, transparent to visible light, has a refractive index compatible with vision by the eye, has an elastic modulus of about 0.01 MPa to about 5.0 MPa, and has a shape compatible with incorporation into the eye.

6. The method of claim 5, wherein the engineered polymer comprises repeated blocks of an elastin domain selected from the group consisting of SEQ ID NO: 2-4, 11, 12-19, or 20 or functional variants thereof having 80% sequence identity to one of SEQ ID NO: 2-4, 11, 12-19, or 20 and combinations thereof.

7. The method of claim 5 or 6, further comprising the step of placing the solution into a mold to form a lens with a shape defined by the mold.

8. A material for use in a mammalian eye, comprising a crosslinked engineered protein which comprises repeated blocks of an elastin domain having one of SEQ ID NO: 2-4, 11, 12-19, and further comprises at least one fibronectin domain having one of SEQ ID NO: 26 and SEQ ID NO: 27, wherein the material is in a shape compatible with incorporation into the eye, biocompatible, transparent to visible light, has a refractive index compatible with vision by the eye, the material is permeable to sufficient nutrients to maintain eye tissue integrity upon incorporation into an eye, and wherein the material forms a hydrogel in water and has an elastic modulus in the hydrogel state of about 0.01 MPa to about 5.0 MPa.

9. A lens comprising a crosslinked engineered protein, which comprises repeated blocks of an elastin domain having the sequence of one of SEQ ID NO: 2-4, 11, 12-19, or 20 or functional variants thereof having 80% sequence identity to one of SEQ ID NO: 2-4, 11, 12-19, or 20, wherein the cross linked engineered protein comprises pentapeptide repeats having the sequence GXGXP (SEQ ID NO: 35), wherein X is any natural, modified, or unusual amino acid, and wherein the lens is optically transparent, resistant to biodegradation, biocompatible, and/or is in a shape suitable for incorporation into the eye.

10. A lens comprising a crosslinked engineered protein, which comprises repeated blocks of an elastin domain and at least one fibronectin domain,
  wherein the elastin domain comprises a sequence of one of SEQ ID NO: 2-4, 11, 12-19, or 20 or functional variants thereof having 80% sequence identity to one of SEQ ID NO: 2-4, 11, 12-19, or 20; and
  the at least one fibronectin domain comprises a sequence of one of SEQ ID NO: 26 or 27 or functional variants thereof having 80% sequence identity to one of SEQ ID NO: 26 or 27, and
  wherein the at least one fibronectin domain further comprises a cell binding domain, and wherein the lens stimulates the adhesion of cells adjacent to said lens.

11. A method of modifying vision of a mammalian eye comprising the step of implanting (i) the lens of claim 9 or 10, or (ii) the material of claim 1, 2 or 3, into a mammal in need thereof, to modify the vision of a mammalian eye.

* * * * *

UNITED STATES PATENT AND TRADEMARK OFFICE
CERTIFICATE OF CORRECTION

| | |
|---|---|
| PATENT NO. | : 8,236,344 B2 |
| APPLICATION NO. | : 11/757990 |
| DATED | : August 7, 2012 |
| INVENTOR(S) | : David A. Tirrell et al. |

It is certified that error appears in the above-identified patent and that said Letters Patent is hereby corrected as shown below:

In the 'Assignee' item (73) of the cover page of the issued patent, the following should appear as an additional assignee:

THE REGENTS OF THE UNIVERSITY OF CALIFORNIA, Oakland, CA (US)

Signed and Sealed this
Fourth Day of December, 2012

David J. Kappos
*Director of the United States Patent and Trademark Office*

SEQUENCE LISTING

```
<160> NUMBER OF SEQ ID NOS: 36

<210> SEQ ID NO 1
<211> LENGTH: 389
<212> TYPE: PRT
<213> ORGANISM: Artificial Sequence
<220> FEATURE:
<223> OTHER INFORMATION: Synthetic Proteins

<400> SEQUENCE: 1

Met Met Ala Ser Met Thr Gly Gly Gln Gln Met Gly His His His His
1               5                   10                  15
```

His His His Asp Asp Asp Lys Leu Asp Tyr Ala Val Thr Gly Arg
            20                  25                  30

Gly Asp Ser Pro Ala Ser Ser Lys Pro Ile Ala Val Pro Gly Ile Gly
        35                  40                  45

Val Pro Gly Ile Gly Val Pro Gly Lys Gly Val Pro Gly Ile Gly Val
50                  55                  60

Pro Gly Ile Gly Val Pro Gly Ile Gly Val Pro Gly Ile Gly Val Pro
65                  70                  75                  80

Gly Lys Gly Val Pro Gly Ile Gly Val Pro Gly Ile Gly Val Pro Gly
            85                  90                  95

Ile Gly Val Pro Gly Ile Gly Val Pro Gly Lys Gly Val Pro Gly Ile
            100                 105                 110

Gly Val Pro Gly Ile Gly Val Pro Gly Ile Gly Val Pro Gly Ile Gly
            115                 120                 125

Val Pro Gly Lys Gly Val Pro Gly Ile Gly Val Pro Gly Ile Gly Val
            130                 135                 140

Pro Leu Asp Tyr Ala Val Thr Gly Arg Gly Asp Ser Pro Ala Ser Ser
145                 150                 155                 160

Lys Pro Ile Ala Val Pro Gly Ile Gly Val Pro Gly Ile Gly Val Pro
            165                 170                 175

Gly Lys Gly Val Pro Gly Ile Gly Val Pro Gly Ile Gly Val Pro Gly
            180                 185                 190

Ile Gly Val Pro Gly Ile Gly Val Pro Gly Lys Gly Val Pro Gly Ile
            195                 200                 205

Gly Val Pro Gly Ile Gly Val Pro Gly Ile Gly Val Pro Gly Ile Gly
            210                 215                 220

Val Pro Gly Lys Gly Val Pro Gly Ile Gly Val Pro Gly Ile Gly Val
225                 230                 235                 240

Pro Gly Ile Gly Val Pro Gly Ile Gly Val Pro Gly Lys Gly Val Pro
            245                 250                 255

Gly Ile Gly Val Pro Gly Ile Gly Val Pro Leu Asp Tyr Ala Val Thr
            260                 265                 270

Gly Arg Gly Asp Ser Pro Ala Ser Ser Lys Pro Ile Ala Val Pro Gly
            275                 280                 285

Ile Gly Val Pro Gly Ile Gly Val Pro Gly Lys Gly Val Pro Gly Ile
            290                 295                 300

Gly Val Pro Gly Ile Gly Val Pro Gly Ile Gly Val Pro Gly Ile Gly
305                 310                 315                 320

Val Pro Gly Lys Gly Val Pro Gly Ile Gly Val Pro Gly Ile Gly Val
            325                 330                 335

Pro Gly Ile Gly Val Pro Gly Ile Gly Val Pro Gly Lys Gly Val Pro
            340                 345                 350

Gly Ile Gly Val Pro Gly Ile Gly Val Pro Gly Ile Gly Val Pro Gly
            355                 360                 365

Ile Gly Val Pro Gly Lys Gly Val Pro Gly Ile Gly Val Pro Gly Ile
            370                 375                 380

Gly Val Pro Leu Glu
385

<210> SEQ ID NO 2
<211> LENGTH: 5
<212> TYPE: PRT
<213> ORGANISM: Artificial Sequence
<220> FEATURE:
<223> OTHER INFORMATION: Synthetic Proteins

```
<400> SEQUENCE: 2

Val Pro Gly Val Gly
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic Proteins

<400> SEQUENCE: 3

Val Pro Gly Lys Gly
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic Proteins

<400> SEQUENCE: 4

Val Pro Gly Ile Gly
1               5

<210> SEQ ID NO 5
<211> LENGTH: 59
<212> TYPE: PRT
<213> ORGANISM: ARTIFICIAL SEQUENCE
<220> FEATURE:
<223> OTHER INFORMATION: Synthetic Proteins

<400> SEQUENCE: 5

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
            20                  25                  30

Gly Ala Gly Ser Gly Ala Gly Ala Gly Ser Gly Ala Gly Ala Gly Ser
        35                  40                  45

Gly Ala Gly Ala Gly Ser Gly Ala Ala Gly Tyr
    50                  55

<210> SEQ ID NO 6
<211> LENGTH: 6
<212> TYPE: PRT
<213> ORGANISM: Artificial Sequence
<220> FEATURE:
<223> OTHER INFORMATION: Synthetic Proteins

<400> SEQUENCE: 6

Gly Ala Gly Ala Gly Ser
1               5

<210> SEQ ID NO 7
<211> LENGTH: 71
<212> TYPE: PRT
<213> ORGANISM: Artificial Sequence
<220> FEATURE:
<223> OTHER INFORMATION: Synthetic Proteins

<400> SEQUENCE: 7

Gly Ala Gly Ala Gly Ser Gly Ala Gly Ala Gly Ser Gly Ala Gly Ala
1               5                   10                  15
```

Gly Ser Gly Ala Gly Ala Gly Ser Gly Ala Gly Ala Gly Ser Gly Ala
            20                  25                  30

Gly Ala Gly Ser Gly Ala Gly Ala Gly Ser Gly Ala Gly Ala Gly Ser
        35                  40                  45

Gly Ala Gly Ala Gly Ser Gly Ala Ala Val Thr Gly Arg Gly Asp Ser
    50                  55                  60

Pro Ala Ser Ala Ala Gly Tyr
65                  70

<210> SEQ ID NO 8
<211> LENGTH: 74
<212> TYPE: PRT
<213> ORGANISM: Artificial Sequence
<220> FEATURE:
<223> OTHER INFORMATION: Synthetic Proteins

<400> SEQUENCE: 8

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
            20                  25                  30

Gly Ala Gly Ser Gly Ala Gly Ala Gly Ser Gly Ala Gly Ala Gly Ser
        35                  40                  45

Gly Ala Gly Ala Gly Ser Gly Ala Ala Pro Gly Ala Ser Ile Lys Val
    50                  55                  60

Ala Val Ser Ala Gly Pro Ser Ala Gly Tyr
65                  70

<210> SEQ ID NO 9
<211> LENGTH: 73
<212> TYPE: PRT
<213> ORGANISM: Artificial Sequence
<220> FEATURE:
<223> OTHER INFORMATION: Synthetic Proteins

<400> SEQUENCE: 9

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
            20                  25                  30

Gly Ala Gly Ser Gly Ala Gly Ala Gly Ser Gly Ala Gly Ala Gly Ser
        35                  40                  45

Gly Ala Gly Ala Gly Ser Gly Ala Ala Pro Gly Ala Ser Ile Lys Val
    50                  55                  60

Ala Val Ser Gly Pro Ser Ala Gly Tyr
65                  70

<210> SEQ ID NO 10
<211> LENGTH: 71
<212> TYPE: PRT
<213> ORGANISM: Artificial Sequence
<220> FEATURE:
<223> OTHER INFORMATION: Synthetic Proteins

<400> SEQUENCE: 10

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
            20                  25                  30

Gly Ala Gly Ser Gly Ala Gly Ala Gly Ser Gly Ala Gly Ala Gly Ser
        35                  40                  45

Gly Ala Gly Ala Gly Ser Arg Tyr Val Val Leu Pro Arg Pro Val Cys
    50                  55                  60

Phe Glu Lys Ala Ala Gly Tyr
65                  70

<210> SEQ ID NO 11
<211> LENGTH: 20
<212> TYPE: PRT
<213> ORGANISM: Artificial Sequence
<220> FEATURE:
<223> OTHER INFORMATION: Synthetic Proteins

<400> SEQUENCE: 11

Val Pro Gly Val Gly Val Pro Gly Val Gly Val Pro Gly Val Gly Val
1               5                   10                  15

Pro Gly Val Gly
            20

<210> SEQ ID NO 12
<211> LENGTH: 52
<212> TYPE: PRT
<213> ORGANISM: Artificial Sequence
<220> FEATURE:
<223> OTHER INFORMATION: Synthetic Proteins

<400> SEQUENCE: 12

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
            20                  25                  30

Gly Val Pro Gly Val Gly Val Pro Gly Ala Gly Ala Gly Ser Gly Ala
        35                  40                  45

Gly Ala Gly Ser
    50

<210> SEQ ID NO 13
<211> LENGTH: 82
<212> TYPE: PRT
<213> ORGANISM: Artificial Sequence
<220> FEATURE:
<223> OTHER INFORMATION: Synthetic Proteins

<400> SEQUENCE: 13

Gly Ala Ala Val Pro Gly Val Gly Val Pro Gly Val Gly Val Pro Gly
1               5                   10                  15

Val Gly Val Pro Gly Val Gly Val Ala Ala Gly Tyr Gly Ala Gly Ala
            20                  25                  30

Gly Ser Gly Ala Gly Ala Gly Ser Gly Ala Gly Ala Gly Ser Gly Ala
        35                  40                  45

Gly Ala Gly Ser Gly Ala Gly Ala Gly Ser Gly Ala Gly Ala Gly Ser
    50                  55                  60

Gly Ala Gly Ala Gly Ser Gly Ala Gly Ala Gly Ser Gly Ala Gly Ala
65                  70                  75                  80

Gly Ser

<210> SEQ ID NO 14
<211> LENGTH: 129
<212> TYPE: PRT
<213> ORGANISM: Artificial Sequence
<220> FEATURE:
<223> OTHER INFORMATION: Synthetic Proteins

```
<400> SEQUENCE: 14

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
            20                  25                  30

Gly Ala Gly Ser Gly Ala Ala Gly Tyr Gly Ala Gly Ala Gly Ser Gly
        35                  40                  45

Ala Gly Ala Gly Ser Gly Ala Gly Ala Gly Ser Gly Ala Gly Ala Gly
    50                  55                  60

Ser Gly Ala Gly Ala Gly Ser Gly Ala Gly Ala Gly Ser Gly Ala Gly
65                  70                  75                  80

Ala Gly Ser Gly Ala Gly Ala Gly Ser Gly Val Gly Val Pro Gly Val
            85                  90                  95

Gly Val Pro Gly Val Gly Val Pro Gly Val Gly Val Pro Gly Val Gly
            100                 105                 110

Val Pro Gly Val Gly Val Pro Gly Val Gly Val Pro Gly Val Gly Val
            115                 120                 125

Pro

<210> SEQ ID NO 15
<211> LENGTH: 88
<212> TYPE: PRT
<213> ORGANISM: Artificial Sequence
<220> FEATURE:
<223> OTHER INFORMATION: Synthetic Proteins

<400> SEQUENCE: 15

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
            20                  25                  30

Gly Val Pro Gly Val Gly Val Pro Gly Ala Gly Ala Gly Ser Gly Ala
            35                  40                  45

Gly Ala Gly Ser Gly Ala Gly Ala Gly Ser Gly Ala Gly Ala Gly Ser
        50                  55                  60

Gly Ala Gly Ala Gly Ser Gly Ala Gly Ala Gly Ser Gly Ala Gly Ala
65                  70                  75                  80

Gly Ser Gly Ala Gly Ala Gly Ser
            85

<210> SEQ ID NO 16
<211> LENGTH: 108
<212> TYPE: PRT
<213> ORGANISM: Artificial Sequence
<220> FEATURE:
<223> OTHER INFORMATION: Synthetic Proteins

<400> SEQUENCE: 16

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
            20                  25                  30

Gly Val Pro Gly Val Gly Val Pro Gly Val Gly Val Pro Gly Val Gly
            35                  40                  45

Val Pro Gly Val Gly Val Pro Gly Val Gly Val Pro Gly Ala Gly Ala
        50                  55                  60

Gly Ser Gly Ala Gly Ala Gly Ser Gly Ala Gly Ala Gly Ser Gly Ala
65                  70                  75                  80
```

```
Gly Ala Gly Ser Gly Ala Gly Ala Gly Ser
            85                  90                  95

Gly Ala Gly Ala Gly Ser Gly Ala Gly Ala Gly Ser
            100                 105

<210> SEQ ID NO 17
<211> LENGTH: 128
<212> TYPE: PRT
<213> ORGANISM: Artificial Sequence
<220> FEATURE:
<223> OTHER INFORMATION: Synthetic Proteins

<400> SEQUENCE: 17

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
            20                  25                  30

Gly Val Pro Gly Val Gly Val Pro Gly Val Gly Val Pro Gly Val Gly
        35                  40                  45

Val Pro Gly Val Gly Val Pro Gly Val Gly Val Pro Gly Val Gly Val
    50                  55                  60

Pro Gly Val Gly Val Pro Gly Val Gly Val Pro Gly Val Gly Val Pro
65                  70                  75                  80

Gly Ala Gly Ala Gly Ser Gly Ala Gly Ala Gly Ser Gly Ala Gly Ala
            85                  90                  95

Gly Ser Gly Ala Gly Ala Gly Ser Gly Ala Gly Ala Gly Ser Gly Ala
            100                 105                 110

Gly Ala Gly Ser Gly Ala Gly Ala Gly Ser Gly Ala Gly Ala Gly Ser
        115                 120                 125

<210> SEQ ID NO 18
<211> LENGTH: 208
<212> TYPE: PRT
<213> ORGANISM: Artificial Sequence
<220> FEATURE:
<223> OTHER INFORMATION: Synthetic Proteins

<400> SEQUENCE: 18

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
            20                  25                  30

Gly Val Pro Gly Val Gly Val Pro Gly Val Gly Val Pro Gly Val Gly
        35                  40                  45

Val Pro Gly Val Gly Val Pro Gly Val Gly Val Pro Gly Val Gly Val
    50                  55                  60

Pro Gly Val Gly Val Pro Gly Val Gly Val Pro Gly Val Gly Val Pro
65                  70                  75                  80

Gly Val Gly Val Pro Gly Val Gly Val Pro Gly Val Gly Val Pro Gly
            85                  90                  95

Val Gly Val Pro Gly Val Gly Val Pro Gly Val Gly Val Pro Gly Val
            100                 105                 110

Gly Val Pro Gly Val Gly Val Pro Gly Val Gly Val Pro Gly Val Gly
        115                 120                 125

Val Pro Gly Val Gly Val Pro Gly Val Gly Val Pro Gly Val Gly Val
    130                 135                 140

Pro Gly Val Gly Val Pro Gly Val Gly Val Pro Gly Val Gly Val Pro
145                 150                 155                 160
```

```
Gly Ala Gly Ala Gly Ser Gly Ala Gly Ala Gly Ser Gly Ala Gly Ala
            165                 170                 175

Gly Ser Gly Ala Gly Ala Gly Ser Gly Ala Gly Ala Gly Ser Gly Ala
        180                 185                 190

Gly Ala Gly Ser Gly Ala Gly Ala Gly Ser Gly Ala Gly Ala Gly Ser
    195                 200                 205

<210> SEQ ID NO 19
<211> LENGTH: 76
<212> TYPE: PRT
<213> ORGANISM: Artificial Sequence
<220> FEATURE:
<223> OTHER INFORMATION: Synthetic Proteins

<400> SEQUENCE: 19

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
            20                  25                  30

Gly Val Pro Gly Val Gly Val Pro Gly Ala Ala Gly Ser Gly Ala
        35                  40                  45

Gly Ala Gly Ser Gly Ala Gly Ala Gly Ser Gly Ala Gly Ala Gly Ser
    50                  55                  60

Gly Ala Gly Ala Gly Ser Gly Ala Gly Ala Gly Ser
65                  70                  75

<210> SEQ ID NO 20
<211> LENGTH: 64
<212> TYPE: PRT
<213> ORGANISM: Artificial Sequence
<220> FEATURE:
<223> OTHER INFORMATION: Synthetic Proteins

<400> SEQUENCE: 20

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
            20                  25                  30

Gly Val Pro Gly Val Gly Val Pro Gly Ala Ala Gly Ser Gly Ala
        35                  40                  45

Gly Ala Gly Ser Gly Ala Gly Ala Gly Ser Gly Ala Gly Ala Gly Ser
    50                  55                  60

<210> SEQ ID NO 21
<211> LENGTH: 56
<212> TYPE: PRT
<213> ORGANISM: Artificial Sequence
<220> FEATURE:
<223> OTHER INFORMATION: Synthetic Proteins

<400> SEQUENCE: 21

Ala Lys Leu Lys Leu Ala Glu Ala Lys Leu Glu Leu Ala Glu Ala Lys
1               5                   10                  15

Leu Lys Leu Ala Glu Ala Lys Leu Glu Leu Ala Glu Ala Lys Leu Lys
            20                  25                  30

Leu Ala Glu Ala Lys Leu Glu Leu Ala Glu Ala Lys Leu Lys Leu Ala
        35                  40                  45

Glu Ala Lys Leu Glu Leu Ala Glu
    50                  55
```

```
<210> SEQ ID NO 22
<211> LENGTH: 15
<212> TYPE: PRT
<213> ORGANISM: Artificial Sequence
<220> FEATURE:
<223> OTHER INFORMATION: Synthetic Proteins

<400> SEQUENCE: 22

Gly Ala Pro Gly Pro Pro Gly Pro Pro Gly Pro Pro Gly Pro Pro
1               5                   10                  15

<210> SEQ ID NO 23
<211> LENGTH: 39
<212> TYPE: PRT
<213> ORGANISM: Artificial Sequence
<220> FEATURE:
<223> OTHER INFORMATION: Synthetic Proteins

<400> SEQUENCE: 23

Gly Ala Pro Gly Pro Pro Gly Pro Pro Gly Pro Pro Gly Pro Pro Gly
1               5                   10                  15

Ala Pro Gly Pro Pro Gly Pro Pro Gly Pro Pro Gly Pro Pro Gly Pro
            20                  25                  30

Ala Gly Pro Val Gly Ser Pro
        35

<210> SEQ ID NO 24
<211> LENGTH: 63
<212> TYPE: PRT
<213> ORGANISM: Artificial Sequence
<220> FEATURE:
<223> OTHER INFORMATION: Synthetic Proteins

<400> SEQUENCE: 24

Gly Ala Pro Gly Pro Pro Gly Pro Pro Gly Pro Pro Gly Pro Pro Gly
1               5                   10                  15

Ala Pro Gly Pro Pro Gly Pro Pro Gly Pro Pro Gly Pro Pro Gly Leu
            20                  25                  30

Pro Gly Pro Lys Gly Asp Arg Gly Asp Ala Gly Pro Lys Gly Ala Asp
        35                  40                  45

Gly Ser Pro Gly Pro Ala Gly Pro Ala Gly Pro Val Gly Ser Pro
    50                  55                  60

<210> SEQ ID NO 25
<211> LENGTH: 15
<212> TYPE: PRT
<213> ORGANISM: Artificial Sequence
<220> FEATURE:
<223> OTHER INFORMATION: Synthetic Proteins

<400> SEQUENCE: 25

Gly Ala Pro Gly Ala Pro Gly Ser Gln Gly Ala Pro Gly Leu Gln
1               5                   10                  15

<210> SEQ ID NO 26
<211> LENGTH: 17
<212> TYPE: PRT
<213> ORGANISM: Artificial Sequence
<220> FEATURE:
<223> OTHER INFORMATION: Synthetic Proteins

<400> SEQUENCE: 26

Tyr Ala Val Thr Gly Arg Gly Asp Ser Pro Ala Ser Ser Lys Pro Ile
1               5                   10                  15

Ala
```

<210> SEQ ID NO 27
<211> LENGTH: 22
<212> TYPE: PRT
<213> ORGANISM: Artificial Sequence
<220> FEATURE:
<223> OTHER INFORMATION: Synthetic Proteins

<400> SEQUENCE: 27

```
Leu Glu Gly Glu Glu Ile Gln Ile Gly His Ile Pro Arg Glu Asp Val
1               5                   10                  15

Asp Tyr His Leu Tyr Pro
            20
```

<210> SEQ ID NO 28
<211> LENGTH: 2355
<212> TYPE: PRT
<213> ORGANISM: Homo sapiens
<220> FEATURE:
<221> NAME/KEY: MISC_FEATURE
<222> LOCATION: (1)..(2355)
<223> OTHER INFORMATION: Human fibronectin

<400> SEQUENCE: 28

```
Met Leu Arg Gly Pro Gly Pro Gly Leu Leu Leu Leu Ala Val Gln Cys
1               5                   10                  15

Leu Gly Thr Ala Val Pro Ser Thr Gly Ala Ser Lys Ser Lys Arg Gln
                20                  25                  30

Ala Gln Gln Met Val Gln Pro Gln Ser Pro Val Ala Val Ser Gln Ser
            35                  40                  45

Lys Pro Gly Cys Tyr Asp Asn Gly Lys His Tyr Gln Ile Asn Gln Gln
        50                  55                  60

Trp Glu Arg Thr Tyr Leu Gly Asn Ala Leu Val Cys Thr Cys Tyr Gly
65                  70                  75                  80

Gly Ser Arg Gly Phe Asn Cys Glu Ser Lys Pro Glu Ala Glu Glu Thr
                85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly
    130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
            180                 185                 190

Thr Ser Tyr Val Val Gly Glu Thr Trp Glu Lys Pro Tyr Gln Gly Trp
        195                 200                 205

Met Met Val Asp Cys Thr Cys Leu Gly Glu Gly Ser Gly Arg Ile Thr
    210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                245                 250                 255

Gln Cys Ile Cys Thr Gly Asn Gly Arg Gly Glu Trp Lys Cys Glu Arg
            260                 265                 270
```

```
His Thr Ser Val Gln Thr Thr Ser Ser Gly Ser Gly Pro Phe Thr Asp
        275                 280                 285

Val Arg Ala Ala Val Tyr Gln Pro Gln Pro His Pro Gln Pro Pro Pro
    290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
                325                 330                 335

Gly Asn Gly Val Ser Cys Gln Glu Thr Ala Val Thr Gln Thr Tyr Gly
            340                 345                 350

Gly Asn Ser Asn Gly Glu Pro Cys Val Leu Pro Phe Thr Tyr Asn Gly
        355                 360                 365

Arg Thr Phe Tyr Ser Cys Thr Thr Glu Gly Arg Gln Asp Gly His Leu
    370                 375                 380

Trp Cys Ser Thr Thr Ser Asn Tyr Glu Gln Asp Gln Lys Tyr Ser Phe
385                 390                 395                 400

Cys Thr Asp His Thr Val Leu Val Gln Thr Arg Gly Gly Asn Ser Asn
                405                 410                 415

Gly Ala Leu Cys His Phe Pro Phe Leu Tyr Asn Asn His Asn Tyr Thr
            420                 425                 430

Asp Cys Thr Ser Glu Gly Arg Arg Asp Asn Met Lys Trp Cys Gly Thr
        435                 440                 445

Thr Gln Asn Tyr Asp Ala Asp Gln Lys Phe Gly Phe Cys Pro Met Ala
    450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
                485                 490                 495

Thr Cys Val Gly Asn Gly Arg Gly Glu Trp Thr Cys Ile Ala Tyr Ser
            500                 505                 510

Gln Leu Arg Asp Gln Cys Ile Val Asp Asp Ile Thr Tyr Asn Val Asn
        515                 520                 525

Asp Thr Phe His Lys Arg His Glu Glu Gly His Met Leu Asn Cys Thr
    530                 535                 540

Cys Phe Gly Gln Gly Arg Gly Arg Trp Lys Cys Asp Pro Val Asp Gln
545                 550                 555                 560

Cys Gln Asp Ser Glu Thr Gly Thr Phe Tyr Gln Ile Gly Asp Ser Trp
                565                 570                 575

Glu Lys Tyr Val His Gly Val Arg Tyr Gln Cys Tyr Cys Tyr Gly Arg
            580                 585                 590

Gly Ile Gly Glu Trp His Cys Gln Pro Leu Gln Thr Tyr Pro Ser Ser
        595                 600                 605

Ser Gly Pro Val Glu Val Phe Ile Thr Glu Thr Pro Ser Gln Pro Asn
    610                 615                 620

Ser His Pro Ile Gln Trp Asn Ala Pro Gln Pro Ser His Ile Ser Lys
625                 630                 635                 640

Tyr Ile Leu Arg Trp Arg Pro Lys Asn Ser Val Gly Arg Trp Lys Glu
                645                 650                 655

Ala Thr Ile Pro Gly His Leu Asn Ser Tyr Thr Ile Lys Gly Leu Lys
            660                 665                 670

Pro Gly Val Val Tyr Glu Gly Gln Leu Ile Ser Ile Gln Gln Tyr Gly
        675                 680                 685

His Gln Glu Val Thr Arg Phe Asp Phe Thr Thr Thr Ser Thr Ser Thr
    690                 695                 700
```

```
Pro Val Thr Ser Asn Thr Val Thr Gly Glu Thr Pro Phe Ser Pro
705                 710                 715                 720

Leu Val Ala Thr Ser Glu Ser Val Thr Glu Ile Thr Ala Ser Ser Phe
            725                 730                 735

Val Val Ser Trp Val Ser Ala Ser Asp Thr Val Ser Gly Phe Arg Val
        740                 745                 750

Glu Tyr Glu Leu Ser Glu Glu Gly Asp Glu Pro Gln Tyr Leu Asp Leu
    755                 760                 765

Pro Ser Thr Ala Thr Ser Val Asn Ile Pro Asp Leu Leu Pro Gly Arg
770                 775                 780

Lys Tyr Ile Val Asn Val Tyr Gln Ile Ser Glu Asp Gly Glu Gln Ser
785                 790                 795                 800

Leu Ile Leu Ser Thr Ser Gln Thr Thr Ala Pro Asp Ala Pro Pro Asp
                805                 810                 815

Pro Thr Val Asp Gln Val Asp Asp Thr Ser Ile Val Val Arg Trp Ser
            820                 825                 830

Arg Pro Gln Ala Pro Ile Thr Gly Tyr Arg Ile Val Tyr Ser Pro Ser
        835                 840                 845

Val Glu Gly Ser Ser Thr Glu Leu Asn Leu Pro Glu Thr Ala Asn Ser
    850                 855                 860

Val Thr Leu Ser Asp Leu Gln Pro Gly Val Gln Tyr Asn Ile Thr Ile
865                 870                 875                 880

Tyr Ala Val Glu Glu Asn Gln Glu Ser Thr Pro Val Val Ile Gln Gln
                885                 890                 895

Glu Thr Thr Gly Thr Pro Arg Ser Asp Thr Val Pro Ser Pro Arg Asp
            900                 905                 910

Leu Gln Phe Val Glu Val Thr Asp Val Lys Val Thr Ile Met Trp Thr
        915                 920                 925

Pro Pro Glu Ser Ala Val Thr Gly Tyr Arg Val Asp Val Ile Pro Val
    930                 935                 940

Asn Leu Pro Gly Glu His Gly Gln Arg Leu Pro Ile Ser Arg Asn Thr
945                 950                 955                 960

Phe Ala Glu Val Thr Gly Leu Ser Pro Gly Val Thr Tyr Tyr Phe Lys
                965                 970                 975

Val Phe Ala Val Ser His Gly Arg Glu Ser Lys Pro Leu Thr Ala Gln
            980                 985                 990

Gln Thr Thr Lys Leu Asp Ala Pro Thr Asn Leu Gln Phe Val Asn Glu
        995                 1000                1005

Thr Asp Ser Thr Val Leu Val Arg Trp Thr Pro Pro Arg Ala Gln
1010                1015                1020

Ile Thr Gly Tyr Arg Leu Thr Val Gly Leu Thr Arg Arg Gly Gln
    1025                1030                1035

Pro Arg Gln Tyr Asn Val Gly Pro Ser Val Ser Lys Tyr Pro Leu
    1040                1045                1050

Arg Asn Leu Gln Pro Ala Ser Glu Tyr Thr Val Ser Leu Val Ala
    1055                1060                1065

Ile Lys Gly Asn Gln Glu Ser Pro Lys Ala Thr Gly Val Phe Thr
    1070                1075                1080

Thr Leu Gln Pro Gly Ser Ser Ile Pro Pro Tyr Asn Thr Glu Val
    1085                1090                1095

Thr Glu Thr Thr Ile Val Ile Thr Trp Thr Pro Ala Pro Arg Ile
    1100                1105                1110

Gly Phe Lys Leu Gly Val Arg Pro Ser Gln Gly Gly Glu Ala Pro
```

```
               1115                1120                1125

Arg Glu Val Thr Ser Asp Ser Gly Ser Ile Val Val Ser Gly Leu
        1130                1135                1140

Thr Pro Gly Val Glu Tyr Val Tyr Thr Ile Gln Val Leu Arg Asp
        1145                1150                1155

Gly Gln Glu Arg Asp Ala Pro Ile Val Asn Lys Val Val Thr Pro
        1160                1165                1170

Leu Ser Pro Pro Thr Asn Leu His Leu Glu Ala Asn Pro Asp Thr
        1175                1180                1185

Gly Val Leu Thr Val Ser Trp Glu Arg Ser Thr Thr Pro Asp Ile
        1190                1195                1200

Thr Gly Tyr Arg Ile Thr Thr Thr Pro Thr Asn Gly Gln Gln Gly
        1205                1210                1215

Asn Ser Leu Glu Glu Val Val His Ala Asp Gln Ser Ser Cys Thr
        1220                1225                1230

Phe Asp Asn Leu Ser Pro Gly Leu Glu Tyr Asn Val Ser Val Tyr
        1235                1240                1245

Thr Val Lys Asp Asp Lys Glu Ser Val Pro Ile Ser Asp Thr Ile
        1250                1255                1260

Ile Pro Ala Val Pro Pro Thr Asp Leu Arg Phe Thr Asn Ile
        1265                1270                1275

Gly Pro Asp Thr Met Arg Val Thr Trp Ala Pro Pro Ser Ile
        1280                1285                1290

Asp Leu Thr Asn Phe Leu Val Arg Tyr Ser Pro Val Lys Asn Glu
        1295                1300                1305

Glu Asp Val Ala Glu Leu Ser Ile Ser Pro Ser Asp Asn Ala Val
        1310                1315                1320

Val Leu Thr Asn Leu Leu Pro Gly Thr Glu Tyr Val Val Ser Val
        1325                1330                1335

Ser Ser Val Tyr Glu Gln His Glu Ser Thr Pro Leu Arg Gly Arg
        1340                1345                1350

Gln Lys Thr Gly Leu Asp Ser Pro Thr Gly Ile Asp Phe Ser Asp
        1355                1360                1365

Ile Thr Ala Asn Ser Phe Thr Val His Trp Ile Ala Pro Arg Ala
        1370                1375                1380

Thr Ile Thr Gly Tyr Arg Ile Arg His His Pro Glu His Phe Ser
        1385                1390                1395

Gly Arg Pro Arg Glu Asp Arg Val Pro His Ser Arg Asn Ser Ile
        1400                1405                1410

Thr Leu Thr Asn Leu Thr Pro Gly Thr Glu Tyr Val Val Ser Ile
        1415                1420                1425

Val Ala Leu Asn Gly Arg Glu Glu Ser Pro Leu Leu Ile Gly Gln
        1430                1435                1440

Gln Ser Thr Val Ser Asp Val Pro Arg Asp Leu Glu Val Val Ala
        1445                1450                1455

Ala Thr Pro Thr Ser Leu Leu Ile Ser Trp Asp Ala Pro Ala Val
        1460                1465                1470

Thr Val Arg Tyr Tyr Arg Ile Thr Tyr Gly Glu Thr Gly Gly Asn
        1475                1480                1485

Ser Pro Val Gln Glu Phe Thr Val Pro Gly Ser Lys Ser Thr Ala
        1490                1495                1500

Thr Ile Ser Gly Leu Lys Pro Gly Val Asp Tyr Thr Ile Thr Val
        1505                1510                1515
```

-continued

Tyr Ala Val Thr Gly Arg Gly Asp Ser Pro Ala Ser Ser Lys Pro
1520                1525                1530

Ile Ser Ile Asn Tyr Arg Thr Glu Ile Asp Lys Pro Ser Gln Met
1535                1540                1545

Gln Val Thr Asp Val Gln Asp Asn Ser Ile Ser Val Lys Trp Leu
1550                1555                1560

Pro Ser Ser Ser Pro Val Thr Gly Tyr Arg Val Thr Thr Thr Pro
1565                1570                1575

Lys Asn Gly Pro Gly Pro Thr Lys Thr Lys Thr Ala Gly Pro Asp
1580                1585                1590

Gln Thr Glu Met Thr Ile Glu Gly Leu Gln Pro Thr Val Glu Tyr
1595                1600                1605

Val Val Ser Val Tyr Ala Gln Asn Pro Ser Gly Glu Ser Gln Pro
1610                1615                1620

Leu Val Gln Thr Ala Val Thr Asn Ile Asp Arg Pro Lys Gly Leu
1625                1630                1635

Ala Phe Thr Asp Val Asp Val Asp Ser Ile Lys Ile Ala Trp Glu
1640                1645                1650

Ser Pro Gln Gly Gln Val Ser Arg Tyr Arg Val Thr Tyr Ser Ser
1655                1660                1665

Pro Glu Asp Gly Ile His Glu Leu Phe Pro Ala Pro Asp Gly Glu
1670                1675                1680

Glu Asp Thr Ala Glu Leu Gln Gly Leu Arg Pro Gly Ser Glu Tyr
1685                1690                1695

Thr Val Ser Val Val Ala Leu His Asp Asp Met Glu Ser Gln Pro
1700                1705                1710

Leu Ile Gly Thr Gln Ser Thr Ala Ile Pro Ala Pro Thr Asp Leu
1715                1720                1725

Lys Phe Thr Gln Val Thr Pro Thr Ser Leu Ser Ala Gln Trp Thr
1730                1735                1740

Pro Pro Asn Val Gln Leu Thr Gly Tyr Arg Val Arg Val Thr Pro
1745                1750                1755

Lys Glu Lys Thr Gly Pro Met Lys Glu Ile Asn Leu Ala Pro Asp
1760                1765                1770

Ser Ser Ser Val Val Val Ser Gly Leu Met Val Ala Thr Lys Tyr
1775                1780                1785

Glu Val Ser Val Tyr Ala Leu Lys Asp Thr Leu Thr Ser Arg Pro
1790                1795                1800

Ala Gln Gly Val Val Thr Thr Leu Glu Asn Val Ser Pro Pro Arg
1805                1810                1815

Arg Ala Arg Val Thr Asp Ala Thr Glu Thr Thr Ile Thr Ile Ser
1820                1825                1830

Trp Arg Thr Lys Thr Glu Thr Ile Thr Gly Phe Gln Val Asp Ala
1835                1840                1845

Val Pro Ala Asn Gly Gln Thr Pro Ile Gln Arg Thr Ile Lys Pro
1850                1855                1860

Asp Val Arg Ser Tyr Thr Ile Thr Gly Leu Gln Pro Gly Thr Asp
1865                1870                1875

Tyr Lys Ile Tyr Leu Tyr Thr Leu Asn Asp Asn Ala Arg Ser Ser
1880                1885                1890

Pro Val Val Ile Asp Ala Ser Thr Ala Ile Asp Ala Pro Ser Asn
1895                1900                1905

Leu Arg Phe Leu Ala Thr Thr Pro Asn Ser Leu Leu Val Ser Trp
1910                1915                1920

```
Gln Pro Pro Arg Ala Arg Ile Thr Gly Tyr Ile Ile Lys Tyr Glu
    1925                1930                1935

Lys Pro Gly Ser Pro Pro Arg Glu Val Val Pro Arg Pro Arg Pro
    1940                1945                1950

Gly Val Thr Glu Ala Thr Ile Thr Gly Leu Glu Pro Gly Thr Glu
    1955                1960                1965

Tyr Thr Ile Tyr Val Ile Ala Leu Lys Asn Asn Gln Lys Ser Glu
    1970                1975                1980

Pro Leu Ile Gly Arg Lys Lys Thr Asp Glu Leu Pro Gln Leu Val
    1985                1990                1995

Thr Leu Pro His Pro Asn Leu His Gly Pro Glu Ile Leu Asp Val
    2000                2005                2010

Pro Ser Thr Val Gln Lys Thr Pro Phe Val Thr His Pro Gly Tyr
    2015                2020                2025

Asp Thr Gly Asn Gly Ile Gln Leu Pro Gly Thr Ser Gly Gln Gln
    2030                2035                2040

Pro Ser Val Gly Gln Gln Met Ile Phe Glu Glu His Gly Phe Arg
    2045                2050                2055

Arg Thr Thr Pro Pro Thr Thr Ala Thr Pro Ile Arg His Arg Pro
    2060                2065                2070

Arg Pro Tyr Pro Pro Asn Val Gly Gln Glu Ala Leu Ser Gln Thr
    2075                2080                2085

Thr Ile Ser Trp Ala Pro Phe Gln Asp Thr Ser Glu Tyr Ile Ile
    2090                2095                2100

Ser Cys His Pro Val Gly Thr Asp Glu Glu Pro Leu Gln Phe Arg
    2105                2110                2115

Val Pro Gly Thr Ser Thr Ser Ala Thr Leu Thr Gly Leu Thr Arg
    2120                2125                2130

Gly Ala Thr Tyr Asn Ile Ile Val Glu Ala Leu Lys Asp Gln Gln
    2135                2140                2145

Arg His Lys Val Arg Glu Glu Val Val Thr Val Gly Asn Ser Val
    2150                2155                2160

Asn Glu Gly Leu Asn Gln Pro Thr Asp Asp Ser Cys Phe Asp Pro
    2165                2170                2175

Tyr Thr Val Ser His Tyr Ala Val Gly Asp Glu Trp Glu Arg Met
    2180                2185                2190

Ser Glu Ser Gly Phe Lys Leu Leu Cys Gln Cys Leu Gly Phe Gly
    2195                2200                2205

Ser Gly His Phe Arg Cys Asp Ser Ser Arg Trp Cys His Asp Asn
    2210                2215                2220

Gly Val Asn Tyr Lys Ile Gly Glu Lys Trp Asp Arg Gln Gly Glu
    2225                2230                2235

Asn Gly Gln Met Met Ser Cys Thr Cys Leu Gly Asn Gly Lys Gly
    2240                2245                2250

Glu Phe Lys Cys Asp Pro His Glu Ala Thr Cys Tyr Asp Asp Gly
    2255                2260                2265

Lys Thr Tyr His Val Gly Glu Gln Trp Gln Lys Glu Tyr Leu Gly
    2270                2275                2280

Ala Ile Cys Ser Cys Thr Cys Phe Gly Gly Gln Arg Gly Trp Arg
    2285                2290                2295

Cys Asp Asn Cys Arg Arg Pro Gly Gly Glu Pro Ser Pro Glu Gly
    2300                2305                2310

Thr Thr Gly Gln Ser Tyr Asn Gln Tyr Ser Gln Arg Tyr His Gln
```

```
                    2315                2320                2325
Arg  Thr  Asn  Thr  Asn  Val  Asn  Cys  Pro  Ile  Glu  Cys  Phe  Met  Pro
          2330                2335                2340

Leu  Asp  Val  Gln  Ala  Asp  Arg  Glu  Asp  Ser  Arg  Glu
     2345                2350                2355

<210> SEQ ID NO 29
<211> LENGTH: 757
<212> TYPE: PRT
<213> ORGANISM: Homo sapiens
<220> FEATURE:
<221> NAME/KEY: MISC_FEATURE
<222> LOCATION: (1)..(757)
<223> OTHER INFORMATION: human elastin

<400> SEQUENCE: 29

Met  Ala  Gly  Leu  Thr  Ala  Ala  Pro  Arg  Pro  Gly  Val  Leu  Leu  Leu
1                   5                   10                  15

Leu  Leu  Ser  Ile  Leu  His  Pro  Ser  Arg  Pro  Gly  Gly  Val  Pro  Gly
               20                  25                  30

Ile  Pro  Gly  Gly  Val  Pro  Gly  Gly  Val  Phe  Tyr  Pro  Gly  Ala  Gly  Leu
          35                  40                  45

Gly  Ala  Leu  Gly  Gly  Gly  Ala  Leu  Gly  Pro  Gly  Gly  Lys  Pro  Leu  Lys
     50                  55                  60

Pro  Val  Pro  Gly  Gly  Leu  Ala  Gly  Ala  Gly  Leu  Gly  Ala  Gly  Leu  Gly
65                  70                  75                  80

Ala  Phe  Pro  Ala  Val  Thr  Phe  Pro  Gly  Ala  Leu  Val  Pro  Gly  Gly  Val
               85                  90                  95

Ala  Asp  Ala  Ala  Ala  Ala  Tyr  Lys  Ala  Ala  Lys  Ala  Gly  Ala  Gly  Leu
               100                 105                 110

Gly  Gly  Val  Pro  Gly  Val  Gly  Gly  Leu  Gly  Val  Ser  Ala  Gly  Ala  Val
               115                 120                 125

Val  Pro  Gln  Pro  Gly  Ala  Gly  Val  Lys  Pro  Gly  Lys  Val  Pro  Gly  Val
     130                 135                 140

Gly  Leu  Pro  Gly  Val  Tyr  Pro  Gly  Gly  Val  Leu  Pro  Gly  Ala  Arg  Phe
145                 150                 155                 160

Pro  Gly  Val  Gly  Val  Leu  Pro  Gly  Val  Pro  Thr  Gly  Ala  Gly  Val  Lys
               165                 170                 175

Pro  Lys  Ala  Pro  Gly  Val  Gly  Gly  Ala  Phe  Ala  Gly  Ile  Pro  Gly  Val
               180                 185                 190

Gly  Pro  Phe  Gly  Gly  Pro  Gln  Pro  Gly  Val  Pro  Leu  Gly  Tyr  Pro  Ile
               195                 200                 205

Lys  Ala  Pro  Lys  Leu  Pro  Gly  Gly  Tyr  Gly  Leu  Pro  Tyr  Thr  Thr  Gly
     210                 215                 220

Lys  Leu  Pro  Tyr  Gly  Tyr  Gly  Pro  Gly  Gly  Val  Ala  Gly  Ala  Ala  Gly
225                 230                 235                 240

Lys  Ala  Gly  Tyr  Pro  Thr  Gly  Thr  Gly  Val  Gly  Pro  Gln  Ala  Ala  Ala
               245                 250                 255

Ala  Ala  Ala  Ala  Lys  Ala  Ala  Lys  Phe  Gly  Ala  Gly  Ala  Ala  Gly
               260                 265                 270

Val  Leu  Pro  Gly  Val  Gly  Gly  Ala  Gly  Val  Pro  Gly  Val  Pro  Gly  Ala
               275                 280                 285

Ile  Pro  Gly  Ile  Gly  Gly  Ile  Ala  Gly  Val  Gly  Thr  Pro  Ala  Ala  Ala
               290                 295                 300

Ala  Ala  Ala  Ala  Ala  Ala  Ala  Lys  Ala  Ala  Lys  Tyr  Gly  Ala  Ala  Ala
305                 310                 315                 320
```

-continued

```
Gly Leu Val Pro Gly Pro Gly Phe Gly Pro Val Val Gly Val
            325                 330             335
Pro Gly Ala Gly Val Pro Val Gly Val Pro Gly Ala Gly Ile Pro
            340                 345             350
Val Val Pro Gly Ala Gly Ile Pro Gly Ala Ala Val Pro Gly Val
            355                 360             365
Ser Pro Glu Ala Ala Ala Lys Ala Ala Lys Ala Ala Lys Tyr Gly
            370                 375             380
Ala Arg Pro Gly Val Gly Val Gly Gly Ile Pro Thr Tyr Gly Val Gly
385                 390                 395             400
Ala Gly Gly Phe Pro Gly Phe Gly Val Gly Val Gly Gly Ile Pro Gly
                405                 410             415
Val Ala Gly Val Pro Ser Val Gly Gly Val Pro Gly Val Gly Gly Val
            420                 425             430
Pro Gly Val Gly Ile Ser Pro Glu Ala Gln Ala Ala Ala Ala Lys
            435                 440             445
Ala Ala Lys Tyr Gly Val Gly Thr Pro Ala Ala Ala Ala Lys Ala
            450                 455             460
Ala Ala Lys Ala Ala Gln Phe Gly Leu Val Pro Gly Val Gly Val Ala
465                 470                 475             480
Pro Gly Val Gly Val Ala Pro Gly Val Gly Val Ala Pro Gly Val Gly
                485                 490             495
Leu Ala Pro Gly Val Gly Val Ala Pro Gly Val Gly Val Ala Pro Gly
            500                 505             510
Val Gly Val Ala Pro Gly Ile Gly Pro Gly Gly Val Ala Ala Ala
            515                 520             525
Lys Ser Ala Ala Lys Val Ala Ala Lys Ala Gln Leu Arg Ala Ala
530                 535                 540
Gly Leu Gly Ala Gly Ile Pro Gly Leu Gly Val Gly Val Gly Val Pro
545                 550                 555             560
Gly Leu Gly Val Gly Ala Gly Val Pro Gly Leu Gly Val Gly Ala Gly
                565                 570             575
Val Pro Gly Phe Gly Ala Gly Ala Asp Glu Gly Val Arg Arg Ser Leu
            580                 585             590
Ser Pro Glu Leu Arg Glu Gly Asp Pro Ser Ser Gln His Leu Pro
            595                 600             605
Ser Thr Pro Ser Ser Pro Arg Val Pro Gly Ala Leu Ala Ala Lys
            610                 615             620
Ala Ala Lys Tyr Gly Ala Ala Val Pro Gly Val Leu Gly Gly Leu Gly
625                 630                 635             640
Ala Leu Gly Gly Val Gly Ile Pro Gly Gly Val Val Gly Ala Gly Pro
                645                 650             655
Ala Ala Ala Ala Ala Ala Ala Lys Ala Ala Lys Ala Ala Gln Phe
            660                 665             670
Gly Leu Val Gly Ala Ala Gly Leu Gly Gly Leu Gly Val Gly Gly Leu
            675                 680             685
Gly Val Pro Gly Val Gly Gly Leu Gly Gly Ile Pro Pro Ala Ala Ala
            690                 695             700
Ala Lys Ala Ala Lys Tyr Gly Ala Ala Gly Leu Gly Gly Val Leu Gly
705                 710                 715             720
Gly Ala Gly Gln Phe Pro Leu Gly Gly Val Ala Ala Arg Pro Gly Phe
                725                 730             735
Gly Leu Ser Pro Ile Phe Pro Gly Gly Ala Cys Leu Gly Lys Ala Cys
            740                 745             750
```

Gly Arg Lys Arg Lys
         755

<210> SEQ ID NO 30
<211> LENGTH: 5
<212> TYPE: PRT
<213> ORGANISM: Artificial Sequence
<220> FEATURE:
<223> OTHER INFORMATION: Synthetic proteins
<220> FEATURE:
<221> NAME/KEY: misc_feature
<222> LOCATION: (4)..(4)
<223> OTHER INFORMATION: Xaa can be any naturally occurring amino acid

<400> SEQUENCE: 30

Val Pro Gly Xaa Gly
1               5

<210> SEQ ID NO 31
<211> LENGTH: 5
<212> TYPE: PRT
<213> ORGANISM: Artificial Sequence
<220> FEATURE:
<223> OTHER INFORMATION: Synthetic proteins

<400> SEQUENCE: 31

Pro Pro Gly Val Gly
1               5

<210> SEQ ID NO 32
<211> LENGTH: 5
<212> TYPE: PRT
<213> ORGANISM: Artificial Sequence
<220> FEATURE:
<223> OTHER INFORMATION: Synthetic protein

<400> SEQUENCE: 32

Gly Val Gly Val Pro
1               5

<210> SEQ ID NO 33
<211> LENGTH: 5
<212> TYPE: PRT
<213> ORGANISM: Artificial Sequence
<220> FEATURE:
<223> OTHER INFORMATION: Synthetic proteins

<400> SEQUENCE: 33

Gly Val Gly Pro Pro
1               5

<210> SEQ ID NO 34
<211> LENGTH: 306
<212> TYPE: PRT
<213> ORGANISM: Artificial sequence
<220> FEATURE:
<223> OTHER INFORMATION: Synthetic proteins

<400> SEQUENCE: 34

Val Pro Gly Ile Gly Val Pro Gly Ile Gly Val Pro Gly Lys Gly Val
1               5                   10                  15

Pro Gly Ile Gly Val Pro Gly Ile Gly Val Pro Gly Ile Gly Val Pro
                20                  25                  30

Gly Ile Gly Val Pro Gly Lys Gly Val Pro Gly Ile Gly Val Pro Gly
            35                  40                  45

Ile Gly Val Pro Gly Ile Gly Val Pro Gly Ile Gly Val Pro Gly Lys

```
                    50                  55                  60
Gly Val Pro Gly Ile Gly Val Pro Gly Ile Gly Val Pro Gly Ile Gly
 65                  70                  75                  80

Val Pro Gly Ile Gly Val Pro Gly Lys Gly Val Pro Gly Ile Gly Val
                 85                  90                  95

Pro Gly Ile Gly Val Pro Val Pro Gly Ile Gly Val Pro Gly Ile Gly
            100                 105                 110

Val Pro Gly Lys Gly Val Pro Gly Ile Gly Val Pro Gly Ile Gly Val
            115                 120                 125

Pro Gly Ile Gly Val Pro Gly Ile Gly Val Pro Gly Lys Gly Val Pro
            130                 135                 140

Gly Ile Gly Val Pro Gly Ile Gly Val Pro Gly Ile Gly Val Pro Gly
145                 150                 155                 160

Ile Gly Val Pro Gly Lys Gly Val Pro Gly Ile Gly Val Pro Gly Ile
                165                 170                 175

Gly Val Pro Gly Ile Gly Val Pro Gly Ile Gly Val Pro Gly Lys Gly
            180                 185                 190

Val Pro Gly Ile Gly Val Pro Gly Ile Gly Val Pro Val Pro Gly Ile
            195                 200                 205

Gly Val Pro Gly Ile Gly Val Pro Gly Lys Gly Val Pro Gly Ile Gly
            210                 215                 220

Val Pro Gly Ile Gly Val Pro Gly Ile Gly Val Pro Gly Ile Gly Val
225                 230                 235                 240

Pro Gly Lys Gly Val Pro Gly Ile Gly Val Pro Gly Ile Gly Val Pro
                245                 250                 255

Gly Ile Gly Val Pro Gly Ile Gly Val Pro Gly Lys Gly Val Pro Gly
            260                 265                 270

Ile Gly Val Pro Gly Ile Gly Val Pro Gly Ile Gly Val Pro Gly Ile
            275                 280                 285

Gly Val Pro Gly Lys Gly Val Pro Gly Ile Gly Val Pro Gly Ile Gly
            290                 295                 300

Val Pro
305

<210> SEQ ID NO 35
<211> LENGTH: 5
<212> TYPE: PRT
<213> ORGANISM: Artificial Sequence
<220> FEATURE:
<223> OTHER INFORMATION: Synthetic proteins
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 35

Gly Xaa Gly Xaa Pro
 1               5

<210> SEQ ID NO 36
<211> LENGTH: 5
<212> TYPE: PRT
<213> ORGANISM: Artificial sequence
```

```
<220> FEATURE:
<223> OTHER INFORMATION: Synthetic proteins

<400> SEQUENCE: 36

Gly Val Gly Pro Pro
1               5
```